United States Patent
Isaka et al.

(10) Patent No.: US 11,099,191 B2
(45) Date of Patent: Aug. 24, 2021

(54) KIDNEY DISEASE PROGNOSIS PREDICTION METHOD AND SYSTEM

(71) Applicants: Osaka University, Suita (JP); Kagami Inc., Ibaraki (JP)

(72) Inventors: Yoshitaka Isaka, Osaka (JP); Tomonori Kimura, Osaka (JP); Keiko Yasuda, Osaka (JP); Kenji Hamase, Fukuoka (JP); Masashi Mita, Tokyo (JP)

(73) Assignees: Osaka University, Osaka (JP); Kagami Inc., Osaka (JP)

( * ) Notice: Subject to any disclaimer, the term of this patent is extended or adjusted under 35 U.S.C. 154(b) by 84 days.

(21) Appl. No.: 16/302,226

(22) PCT Filed: May 17, 2017

(86) PCT No.: PCT/JP2017/018591
§ 371 (c)(1),
(2) Date: Nov. 16, 2018

(87) PCT Pub. No.: WO2017/200024
PCT Pub. Date: Nov. 23, 2017

(65) Prior Publication Data
US 2019/0317106 A1    Oct. 17, 2019

(30) Foreign Application Priority Data
May 17, 2016 (JP) .............. JP2016-099158

(51) Int. Cl.
*G01N 33/68* (2006.01)
*G01N 33/72* (2006.01)

(52) U.S. Cl.
CPC ............. *G01N 33/68* (2013.01); *G01N 33/72* (2013.01); *G01N 2800/347* (2013.01); *G01N 2800/52* (2013.01)

(58) Field of Classification Search
CPC ........ G01N 33/68; G01N 33/50; G01N 33/48; G01N 33/72; G01N 2800/347; G01N 2800/34; G01N 2800/52
USPC ........................................... 436/89
See application file for complete search history.

(56) References Cited

U.S. PATENT DOCUMENTS

2014/0147936 A1 * 5/2014 Hamano ................. G01N 33/82
                                                        436/501
2015/0079623 A1    3/2015 Hamase et al.
2016/0313342 A1   10/2016 Hamase et al.

FOREIGN PATENT DOCUMENTS

| JP | 2003-250582 A | 9/2003 | |
| JP | 2015-132598 A | 7/2015 | |
| WO | WO 2013/140785 A1 | 9/2013 | |
| WO | WO 2015/087985 A1 * | 6/2015 | ........... G01N 33/493 |

OTHER PUBLICATIONS

Fukushima et al. "Determination of D-Amino Acids in Serum from Patients with Renal Dysfunction," Biol. Pharm. Bull, 1995, 18(8):1130-1132.
KDIGO 2012 Clinical Practice Guidelines for the Evaluation and Management of Chronic Kidney Disease, Kidney International Supplements 1, 2013, 3(1):162 pages.
Huang et al., "Urinary Excretion of D-Serine in Human: Comparison of Different Ages and Species," Biol. Pharm. Bull., 1998, 21(2):156-162.
Ishida, Hironori, "Serum D-Amino Acid Elucidated in Renal Failure," Kitasato Medicine, 1993, 23:51-62.
Nagata et al., "Neutral free D-amino acids present in human plasma," Viva Origino, 1990, 18(2):88-89, Collection of Abstracts from the 15th Academic Lecture Presentations, with English translation.
Shlipak et al., "Cystatin C versus Creatinine in Determining Risk Based on Kidney Function," N. Engl. J. Med., 2013, Sep. 5, 2013, 369(10):932-943.
Slocum et al., "Marking renal injury: can we move beyond serum creatinine?", Transl. Res., 2012, 159:277-289.

* cited by examiner

*Primary Examiner* — Christine T Mui
(74) *Attorney, Agent, or Firm* — Foley & Lardner LLP

(57) ABSTRACT

The purpose of the present invention is to provide: a method for predicting the prognosis for kidney disease for a subject on the basis of the amount of D- and L-amino acids, from a blood sample; and an analysis system that determines prognosis predictions. This purpose is achieved by using at least one amino acid to predict the prognosis for kidney disease, said amino acid being selected from the group consisting of D-serine, D-asparagine, D-proline, D-alanine, D-leucine, D-lysine, D-allo-isoleucine, L-glutamic acid, L-alanine, L-tryptophan, and L-asparagine.

21 Claims, 26 Drawing Sheets

FIG. 12
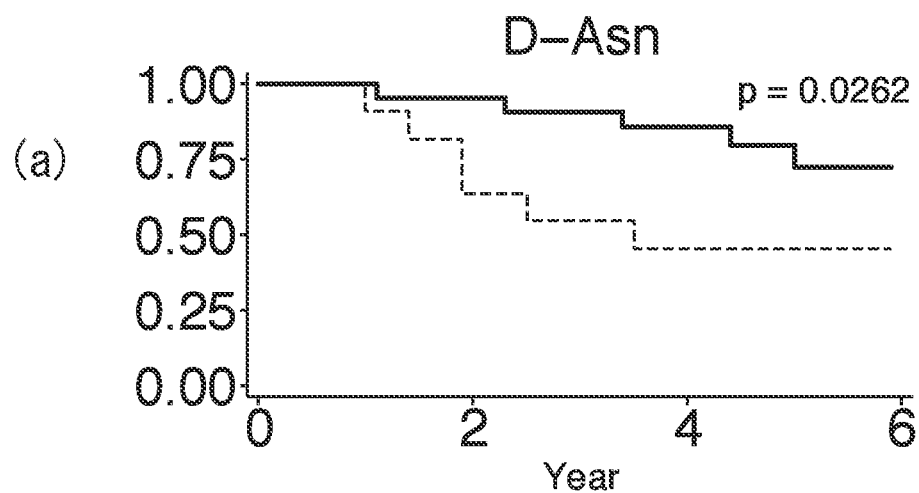
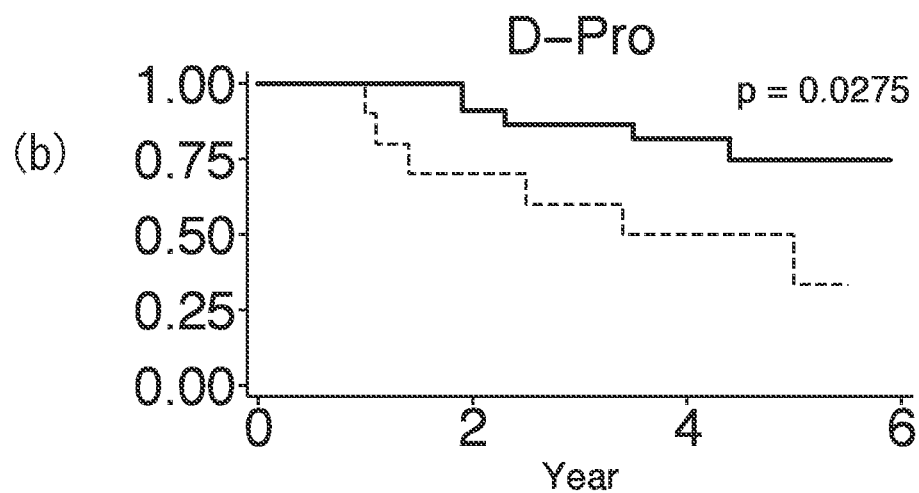

FIG. 16-A
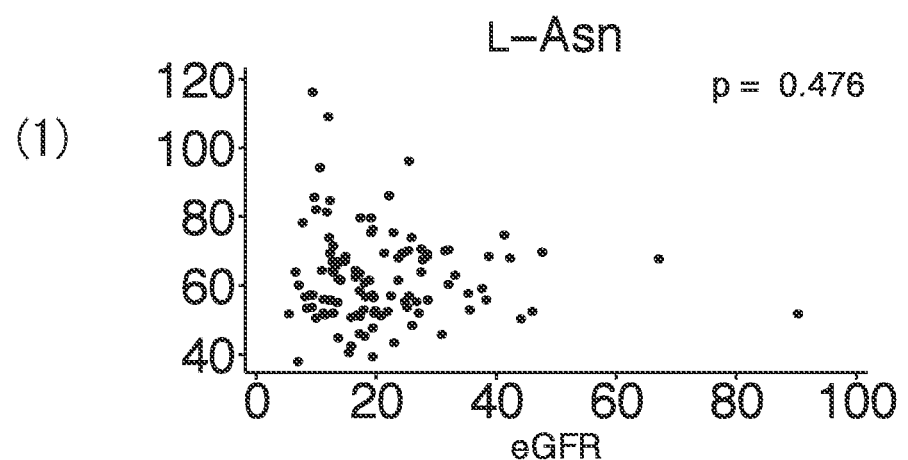
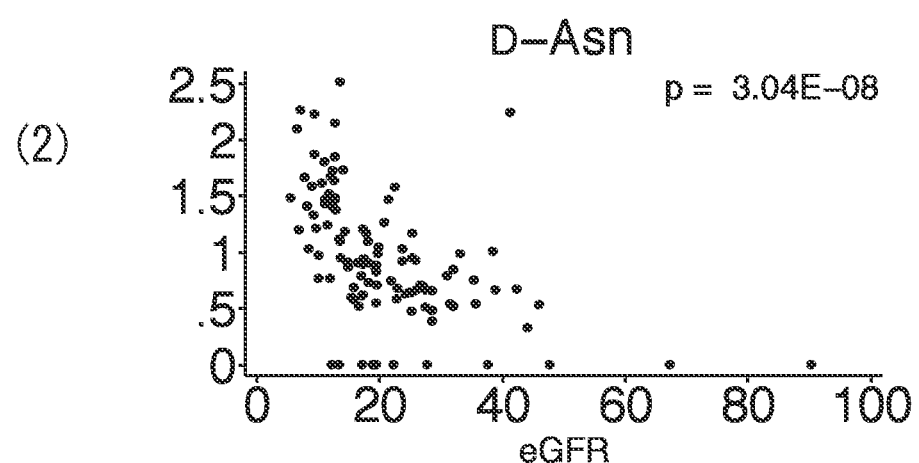
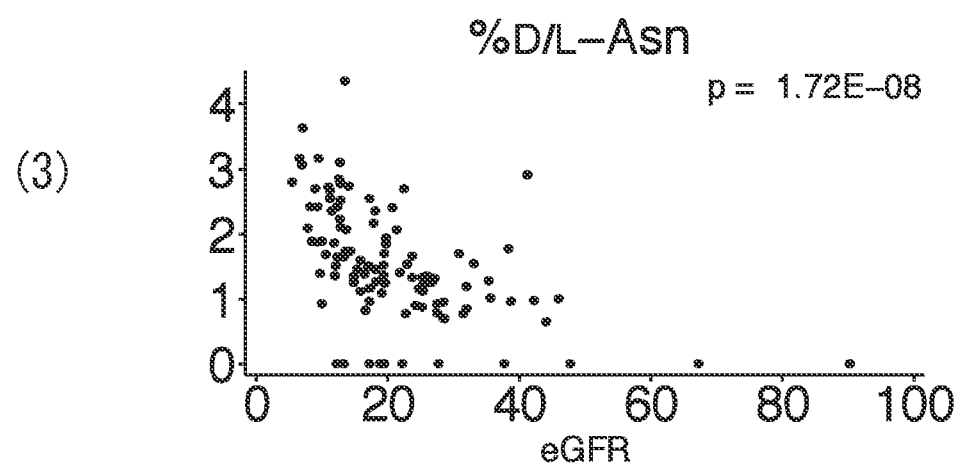

FIG. 16-B
(1) 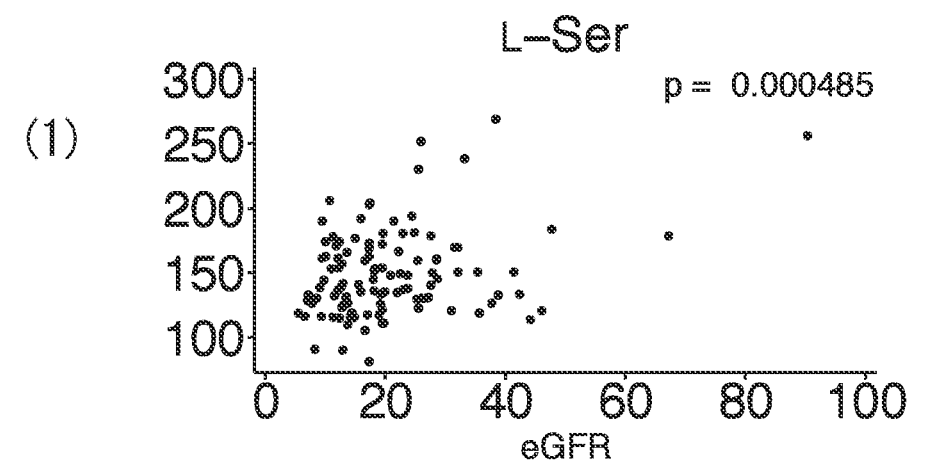
(2) 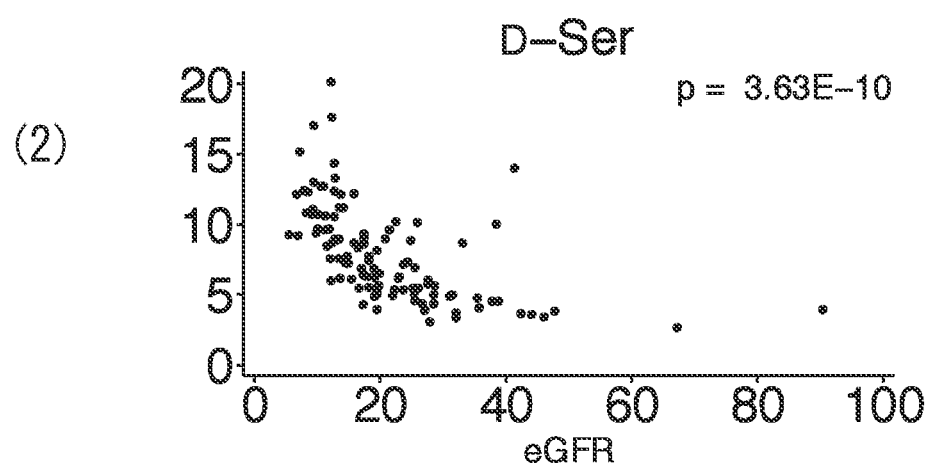
(3) 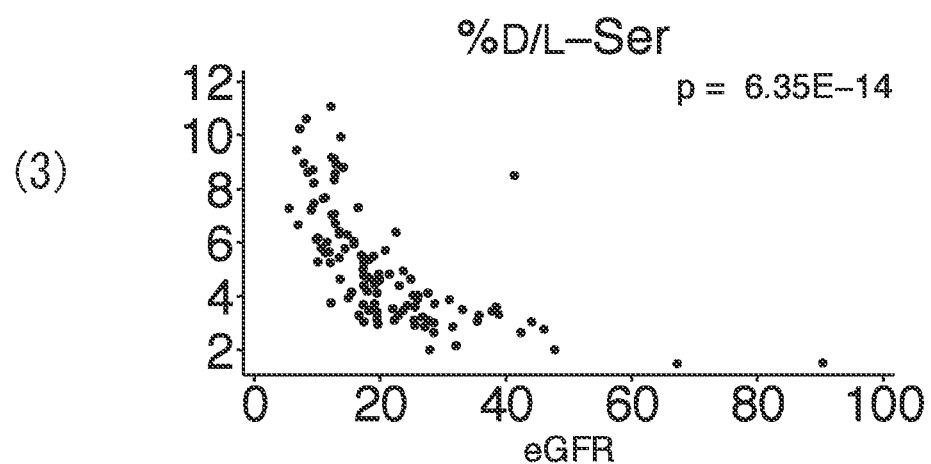

FIG. 16-C
(1) 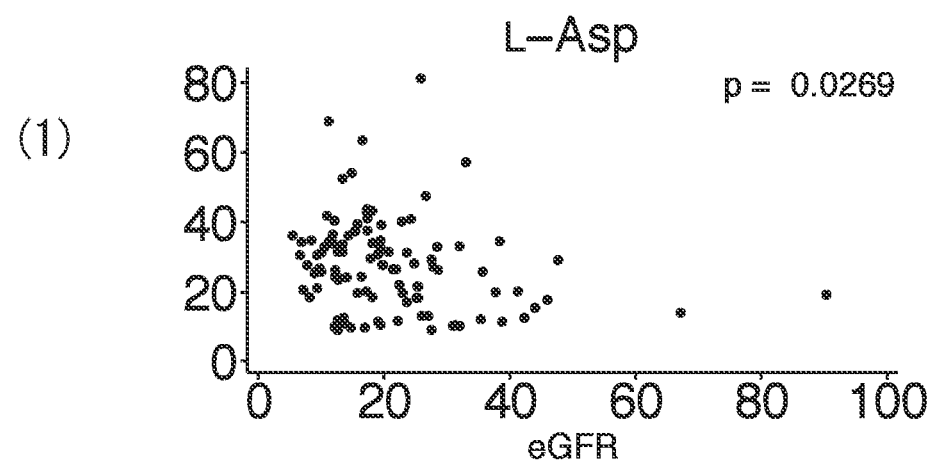
(2) 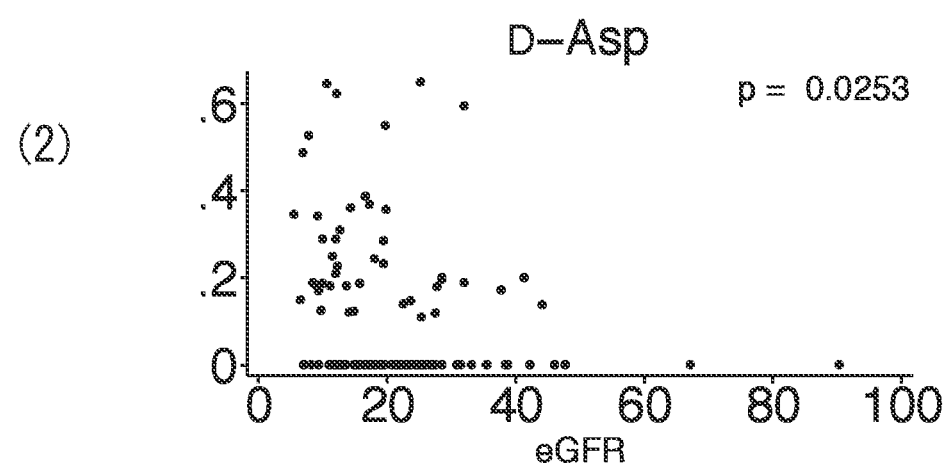
(3) 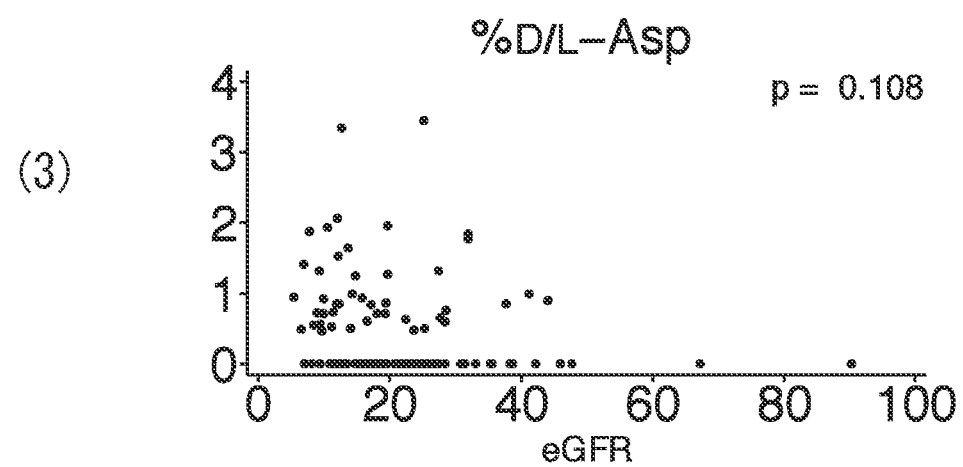

FIG. 16-D
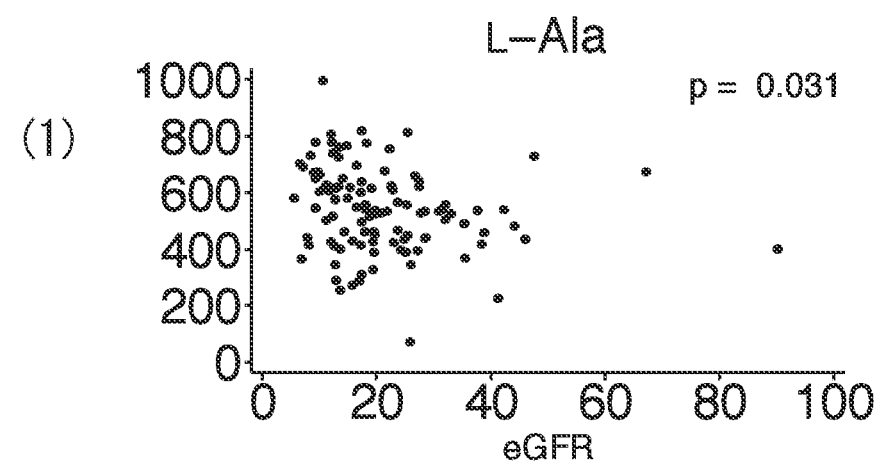
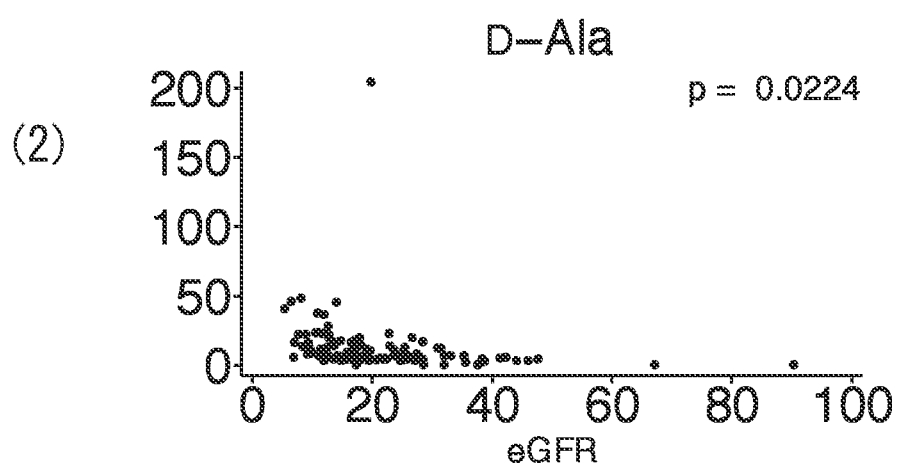
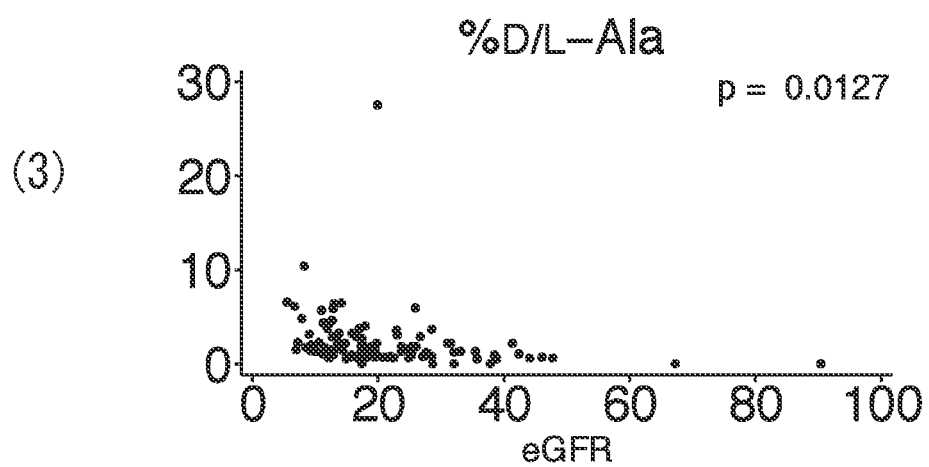

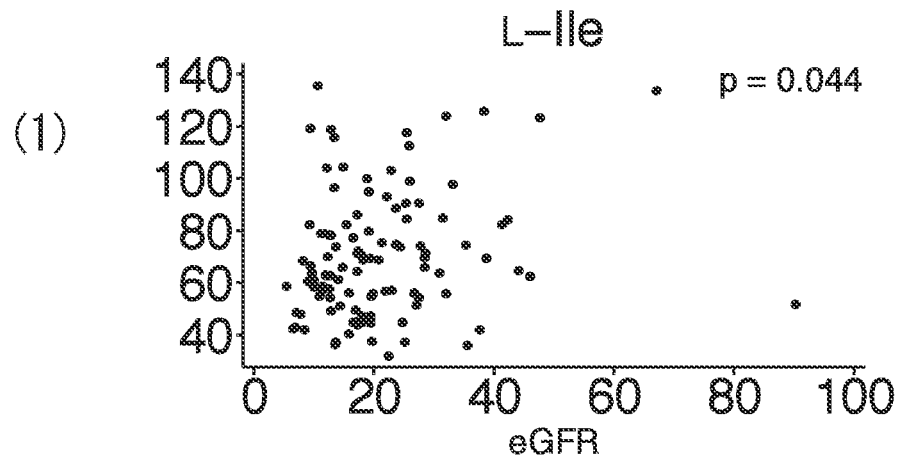
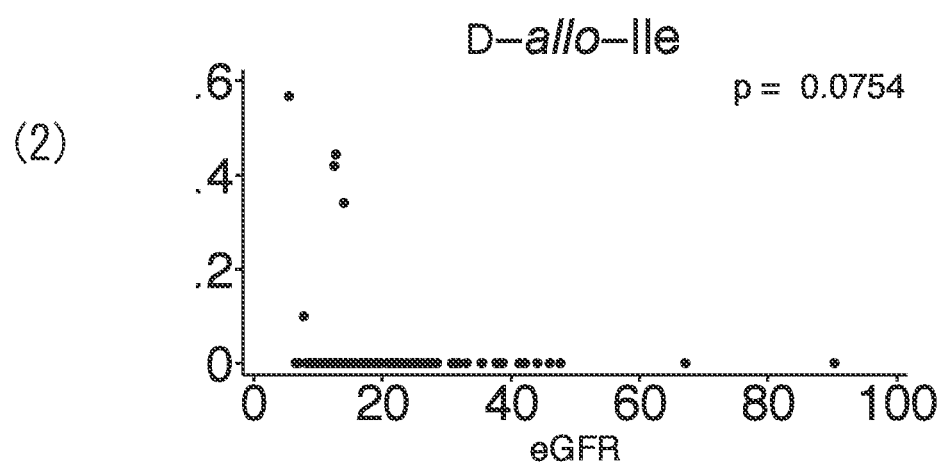
FIG. 16-E

FIG. 16-F
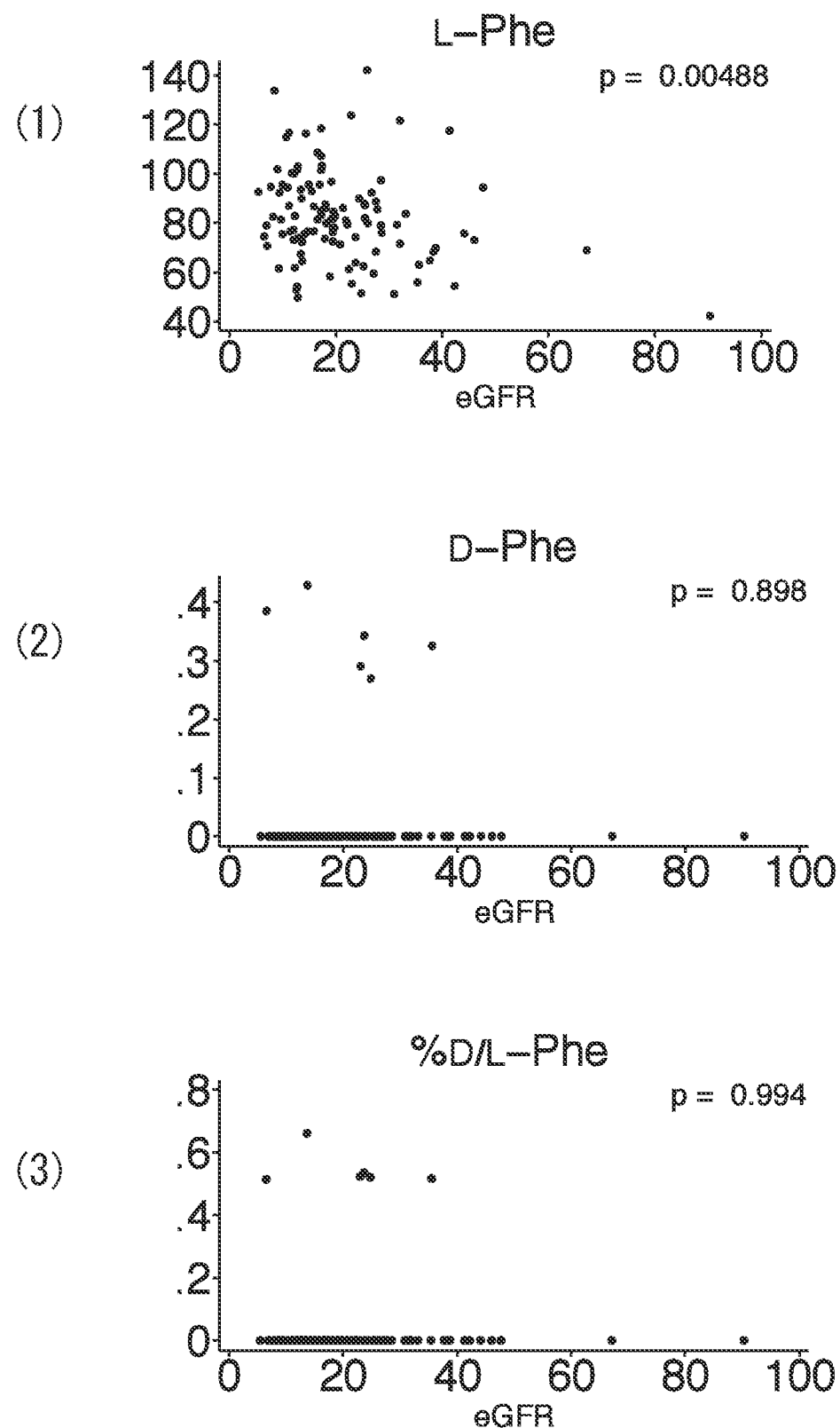

FIG. 16-G
(1) 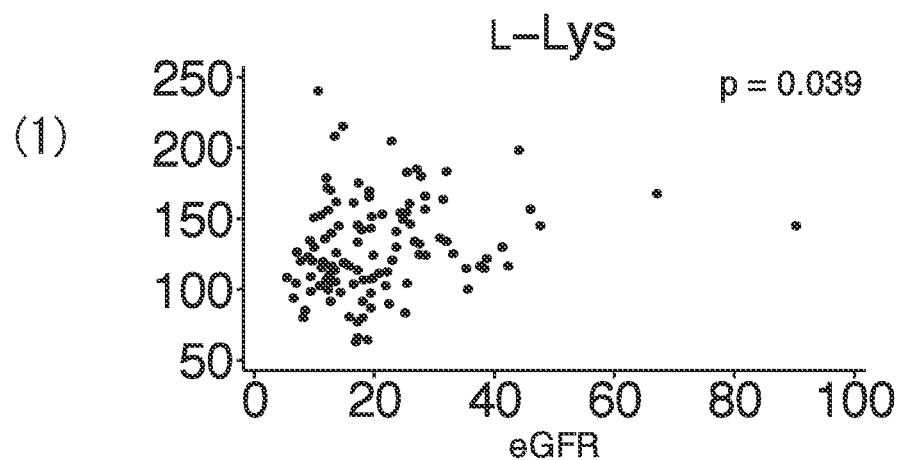
(2) 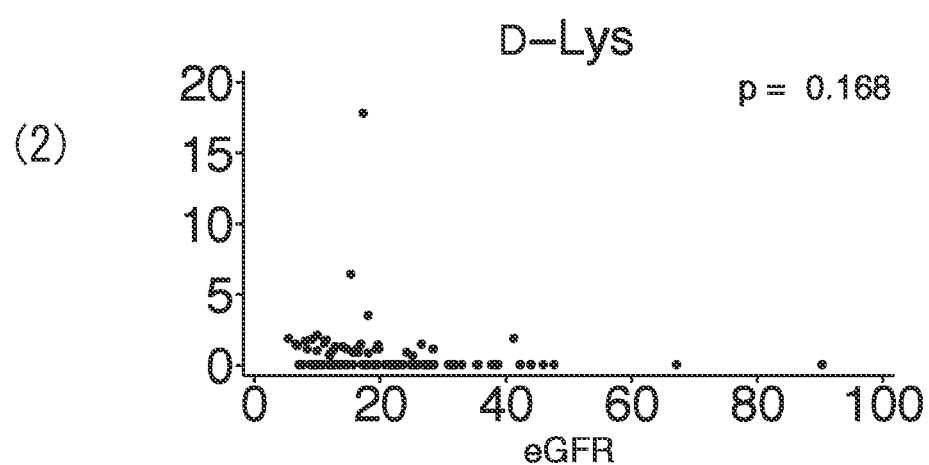
(3) 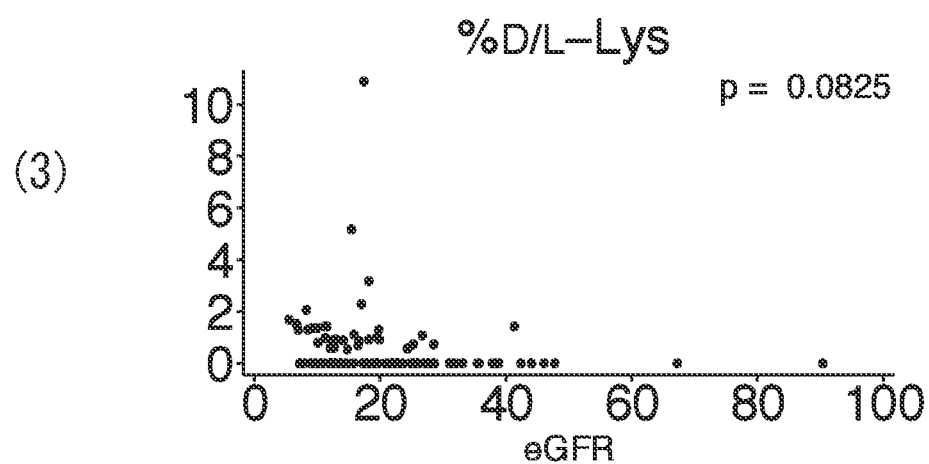

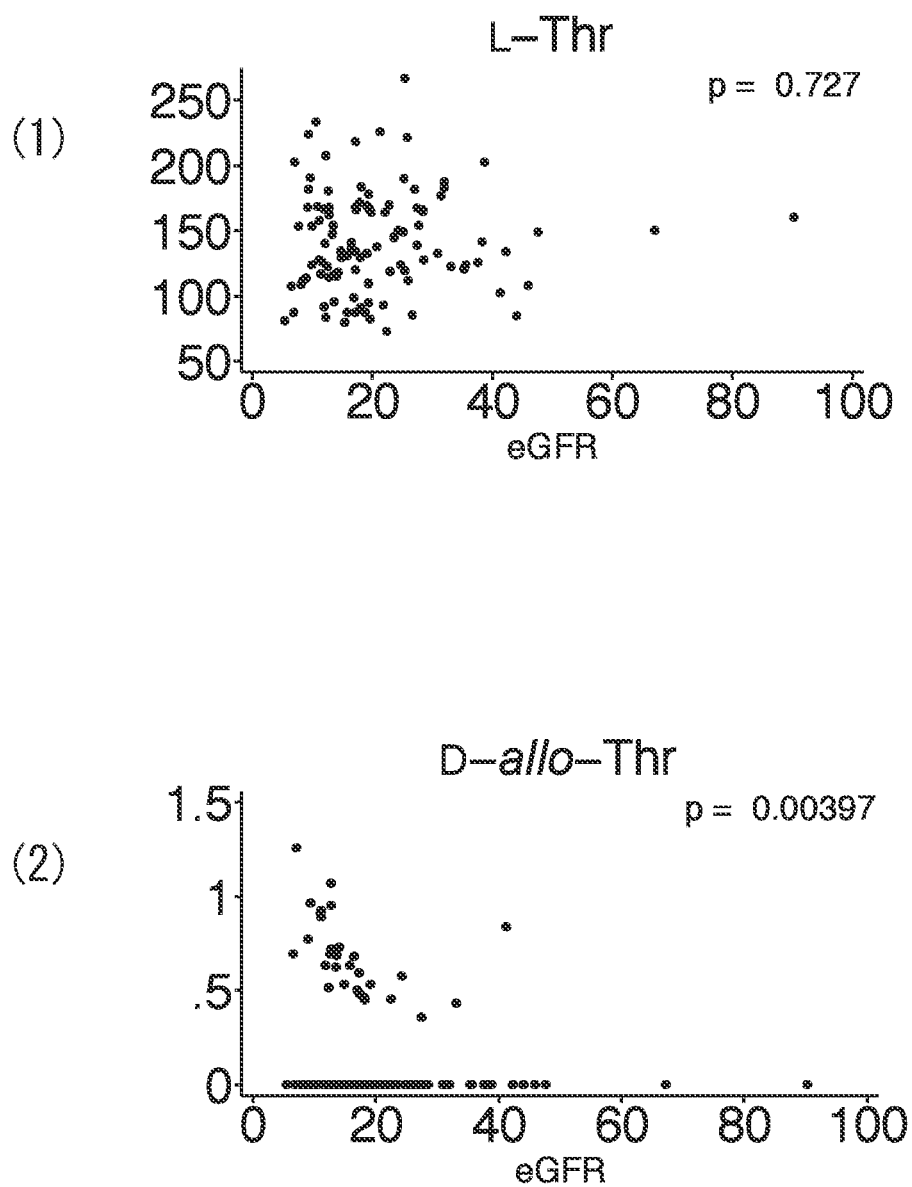

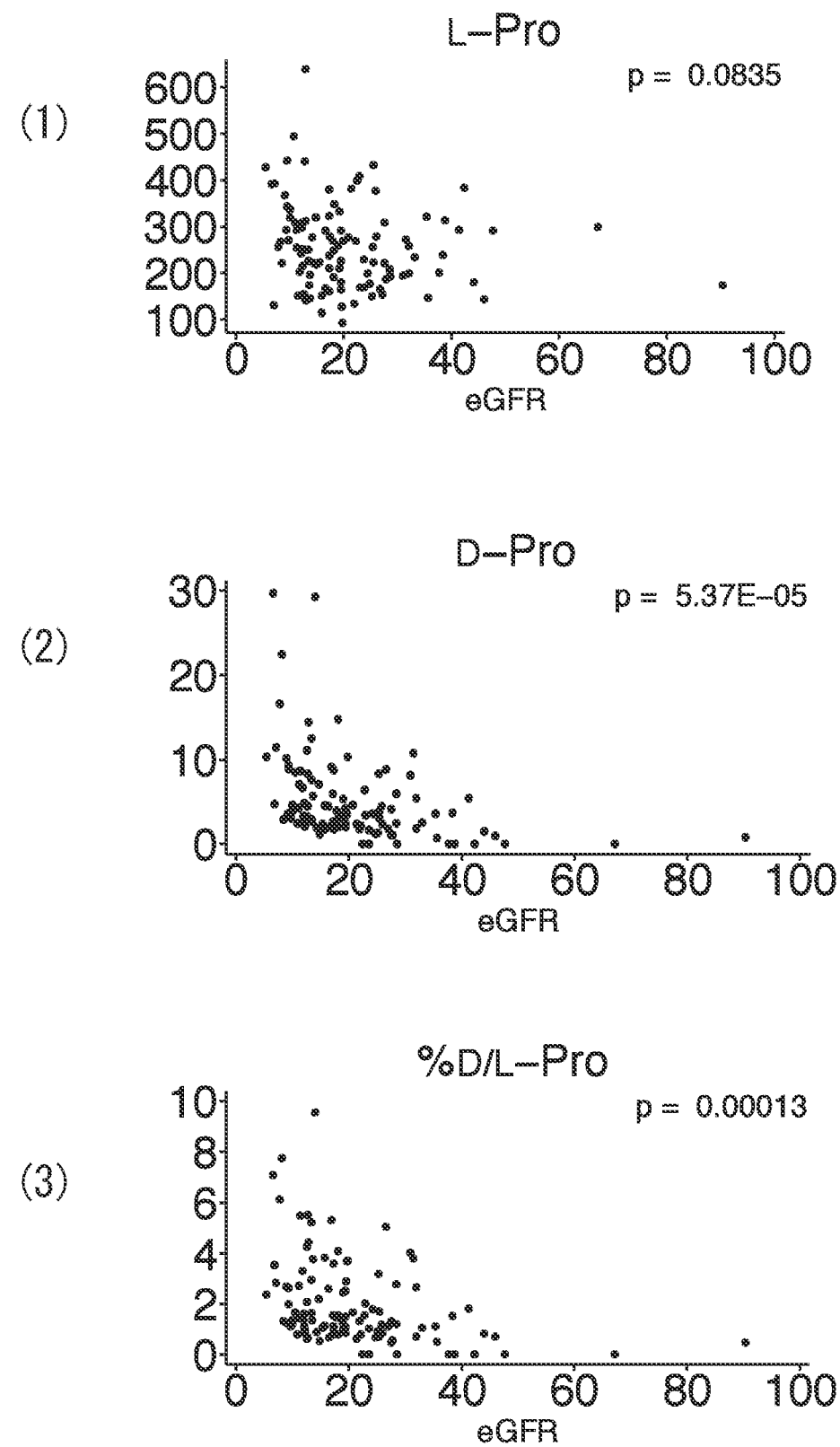
FIG. 16-I

FIG. 16-J
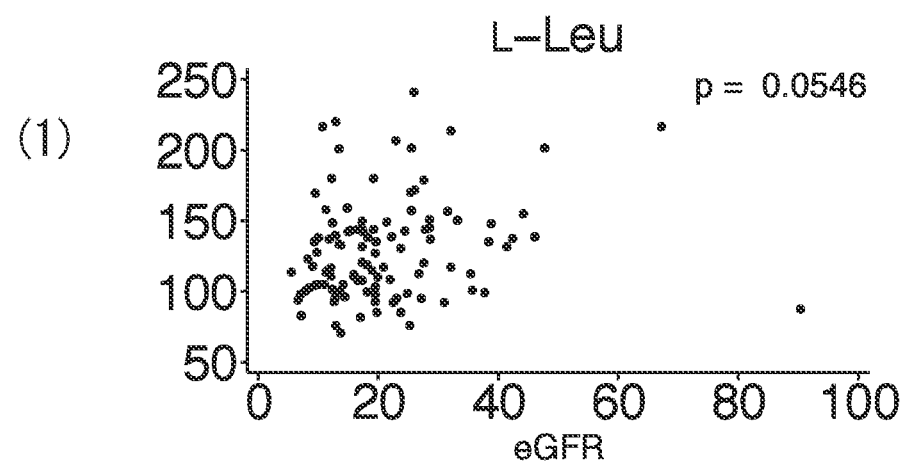
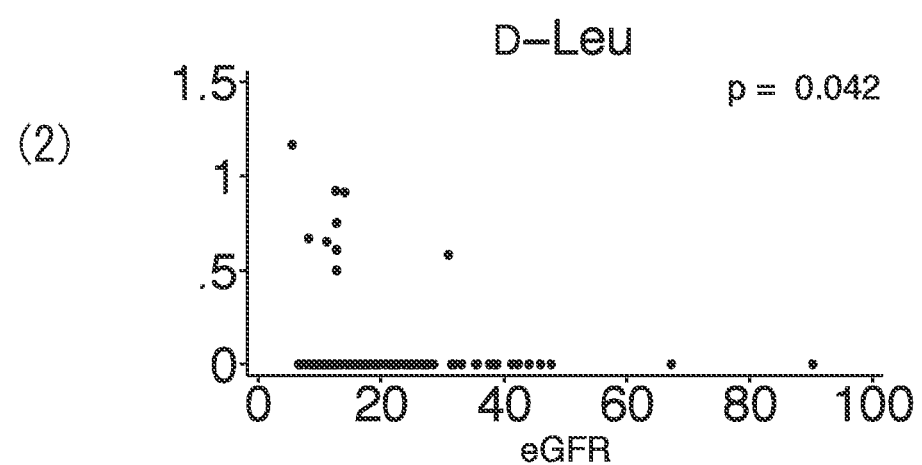
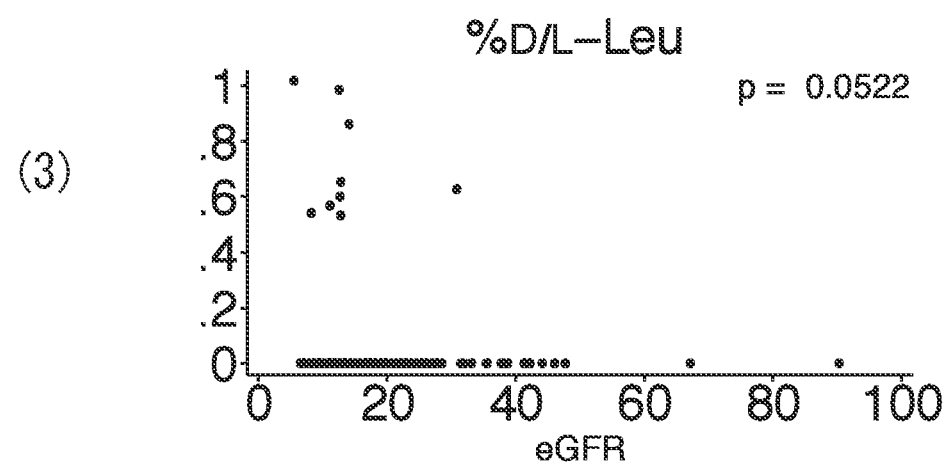

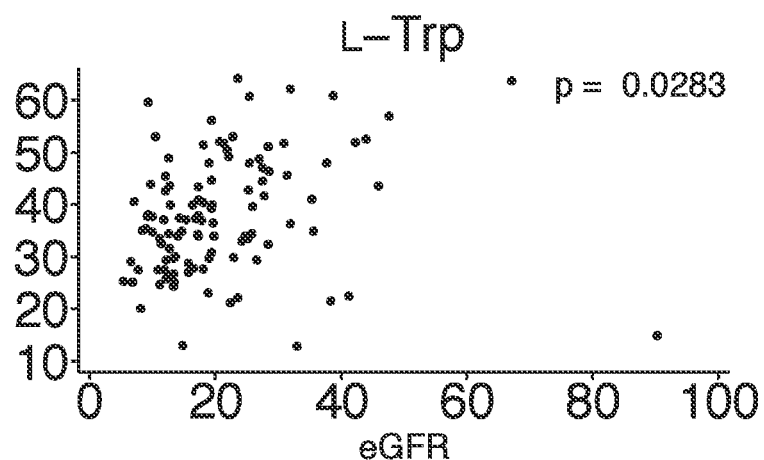
FIG. 16-K
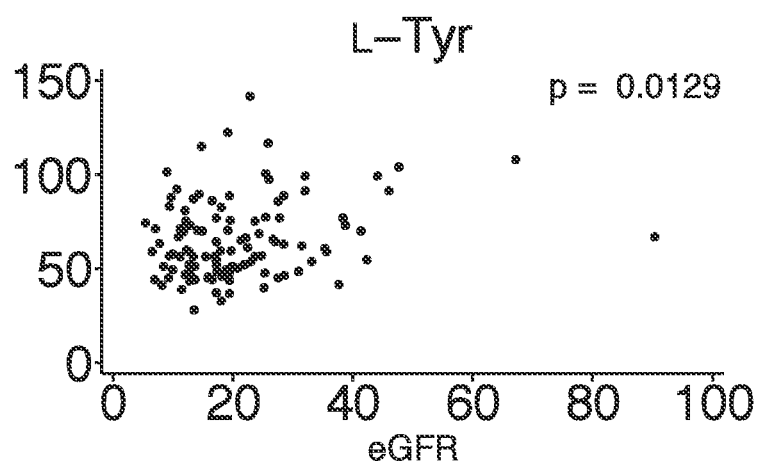
FIG. 16-L

KIDNEY DISEASE PROGNOSIS PREDICTION METHOD AND SYSTEM

CROSS-REFERENCE TO RELATED APPLICATIONS

This application is a National Stage application of PCT/JP2017/018591, filed May 17, 2017, which claims priority to Japanese Patent Application No. 2016-099158, filed May 17, 2016.

FIELD

The present invention relates to a method for predicting a prognosis of kidney disease based on the amounts of D- and/or L-amino acids in a blood sample, and to a prognosis prediction system for kidney disease.

BACKGROUND

The kidney is an organ that filters waste products and excess moisture from the blood and discharges these substances from the body as urine, thereby fulfilling the important role of maintaining homeostasis of the body. The kidneys are damaged by such factors as abnormalities of the immune system, drug allergies, hypertension, diabetes, hemorrhage or sudden drops in blood pressure, infections or burn-induced dehydration, and subsequently undergo a decrease in renal function. Prominent decreases in renal function are referred to as kidney disease, and this is further classified into acute kidney disease (AKD) and chronic kidney disease (CKD) based on the difference in the degree to which the decreased renal function has progressed.

Acute kidney disease (AKD) refers to kidney disease that takes several hours to several weeks until onset of disease. Acute kidney disease is a state in which renal function has suddenly decreased due to a cause such as ischemia, drugs or endotoxin shock. Patients suffering from acute kidney disease are observed to demonstrate elevated blood concentrations of body metabolites in the form of urea nitrogen and creatinine, abnormal metabolism of electrolyte, and asidosis, and acute kidney disease is typically diagnosed by a sudden rise in serum creatinine value. Since patients can be expected to recover from acute kidney disease through treatment, there is a desire for the development of a diagnostic marker that can be used to identify acute kidney disease at an earlier stage. However, since serum creatinine concentration, which has conventionally been used as a diagnostic marker, fluctuates according to conditions such as age, gender, muscle mass and drugs currently being taken, it cannot be said to be a specific diagnostic marker (NPL1). Although proteins such as neutrophil gelatinase-associated lipocalin (NGAL), interleukin-18 (IL-18), kidney injury molecule 1 (KIM-1), fatty acid binding proteins (FABPs) or cystatin C, or metabolic low molecular weight compounds such as homovanillic acid sulfate or trimethylamine-N-oxide have been reported, diagnostic markers that are capable of realizing faster and more accurate detection are expected to be developed.

Chronic kidney disease (CKD) refers to kidney disease in which decreased renal function as represented by glomerular filtration rate, or findings suggestive of kidney damage, chronically persist (for 3 months or more), due to various types of kidney damage. Chronic kidney disease is a disease affecting 13.3 million people in Japan, corresponding to roughly 13% of the adult population, and is considered to constitute a public health threat due to the high risk of progressing to end-stage kidney disease (ESKD). There is no effective treatment for chronic kidney disease, and when chronic kidney disease progresses resulting in decreased renal function, there is the risk of uremia resulting in the need for dialysis or kidney transplant, which are considerable burden in terms of medical care economics (NPL2). Since the pathology of chronic kidney disease progresses without any subjective symptoms, diagnosis based on an early diagnostic marker of kidney disease is required for early detection and inhibition of the progress of chronic kidney disease. However, there are currently no such markers capable of satisfying conditions for use as a diagnostic marker that accurately reflects the progression of kidney disease at an earlier stage due based on the occurrence of changes in renal function as represented by glomerular filtration rate.

Although prediction of the prognosis for kidney disease or the risk thereof is made based on estimated glomerular filtration rate (eGFR) calculated from the value of a kidney disease marker in the form of creatinine or cystatin C, there is a need for the development of a prognosis prediction marker offering higher accuracy (NPL7: New England Journal).

D-amino acids, which have conventionally been considered to not be present in the mammalian body, have recently been determined to be present in various tissues, and are predicted to be responsible for some form of physiological functions. In addition, the concentrations in the blood of D-amino acids consisting of D-serine, D-alanine, D-proline, D-serine, D-glutamic acid and D-aspartic acid have been shown to function as diagnostic markers of kidney disease (NPL3, NPL4, NPL5 and NPL6). Moreover, one or two or more types of amino acids selected from the group consisting of D-serine, D-threonine, D-alanine, D-asparagine, allo-D-threonine, D-glutamine, D-proline and D-phenylalanine have been disclosed to be able to serve as pathological index values of kidney disease (PTL1). However, findings have yet to be obtained regarding the use of D-amino acids to predict prognosis for chronic kidney disease.

CITATION LIST

Patent Literature

[PTL1] WO 2013/140785

Non Patent Literature

[NPL1] Slocum, J. L., et al., Transl. Res. 159: 277 (2012)
[NPL2] KDIGO 2012 Clinical Practice Guidelines for the Evaluation and Management of Chronic Kidney Disease, Kidney International Supplements 1 (2013)
[NPL3] Fukushima, T., et al., Biol. Pharm. Bull. 18: 1130 (1995)
[NPL4] Nagata, Y., Viva Origino Vol. 18 (No. 2) (1990) Collection of Abstracts from the 15th Academic Lecture Presentations
[NPL5] Ishida, et al., Kitasato Medicine 23: 51-62 (1993)
[NPL6] Yong Huang, et al., Biol. Pharm. Bull. 21:(2) 156-162 (1998)
[NPL7] Shlipak, M. G., et al., Cystatin C versus creatinine in determining risk based on kidney function, N. Engl. J. Med., 2013, Sep. 5, 369(10): 932-943

SUMMARY

Technical Problem

There is a desire for the development of a technology for identifying and analyzing a prognosis prediction marker for kidney disease that differs from existing prognosis prediction markers such as glomerular filtration rate or serum creatinine concentration, as well as the development of a technology for accurately determining a prognosis for kidney disease thereby.

Solution to Problem

As a result of analyzing the profiles of chiral amino acids present in blood samples of cohorts, including chronic kidney disease patients, the inventors of the present invention found that patient prognosis can be predicted with high accuracy using several chiral amino acids, thereby leading to completion of the present invention.

Thus, the present invention relates to a method for predicting a prognosis for kidney disease in a subject, comprising:

a step for measuring the amount of chiral amino acids in a blood sample of the subject, and a step for determining a prognosis for kidney disease in the subject based on the amount of chiral amino acids.

In another aspect thereof, the present invention relates to a sample analysis system capable of carrying out the prognosis prediction method of the present invention. This sample analysis system contains a storage unit, an input unit, an analysis/measurement unit, a data processing unit and an output unit, and is able to analyze blood samples and output prognosis information.

In still another aspect, the present invention relates to a program installed in the sample analysis system of the present invention and a storage medium storing that program.

Advantageous Effects of Invention

A prognosis prediction marker can be provided that is able to predict a prognosis for kidney disease based on the amount of chiral amino acids in a blood sample of a subject.

BRIEF DESCRIPTION OF DRAWINGS

FIG. 12 indicates the results of dividing into cohorts including 42 kidney disease patients having eGFR levels of 20 ml/min/1.73 m$^2$ or more, dividing (a) amount of L-asparagine and (b) amount of D-proline at baseline among the cohorts into two tertiles, and subjecting prognoses thereof to a Kaplan-Meier analysis.

FIG. 16-A depicts graphs indicating the correlations between estimated glomerular filtration rate (eGFR) and (1) L-Asn values, (2) D-Asn values and (3) ratio of D/L-Asn values.

FIG. 16-B depicts graphs indicating the correlations between estimated glomerular filtration rate (eGFR) and (1) L-Ser values, (2) D-Ser values and (3) ratio of D/L-Ser values.

FIG. 16-C depicts graphs indicating the correlations between estimated glomerular filtration rate (eGFR) and (1) L-Asp values, (2) D-Asp values and (3) ratio of D/L-Asp values.

FIG. 16-D depicts graphs indicating the correlations between estimated glomerular filtration rate (eGFR) and (1) L-Ala values, (2) D-Ala values and (3) ratio of D/L-Ala values.

FIG. 16-E depicts graphs indicating the correlations between estimated glomerular filtration rate (eGFR) and (1) L-Ile values and (2) D-alloIle values.

FIG. 16-F depicts graphs indicating the correlations between estimated glomerular filtration rate (eGFR) and (1) L-Phe values, (2) D-Phe values and (3) ratio of D/L-Phe values.

FIG. 16-G depicts graphs indicating the correlations between estimated glomerular filtration rate (eGFR) and (1) L-Lys values, (2) D-Lys values and (3) ratio of D/L-Lys values.

FIG. 16-H depicts graphs indicating the correlations between estimated glomerular filtration rate (eGFR) and (1) L-Thr values and (2) D-alloThr values.

FIG. 16-I depicts graphs indicating the correlations between estimated glomerular filtration rate (eGFR) and (1) L-Pro values, (2) D-Pro values and (3) ratio of D/L-Pro values.

FIG. 16-J depicts graphs indicating the correlations between estimated glomerular filtration rate (eGFR) and (1) L-Leu values, (2) D-Leu values and (3) ratio of D/L-Leu values.

FIG. 16-K depicts graphs indicating the correlations between estimated glomerular filtration rate (eGFR) and (1) L-Trp values.

FIG. 16-L depicts graphs indicating the correlations between estimated glomerular filtration rate (eGFR) and (1) L-Tyr values.

DESCRIPTION OF EMBODIMENTS

Figure 1:
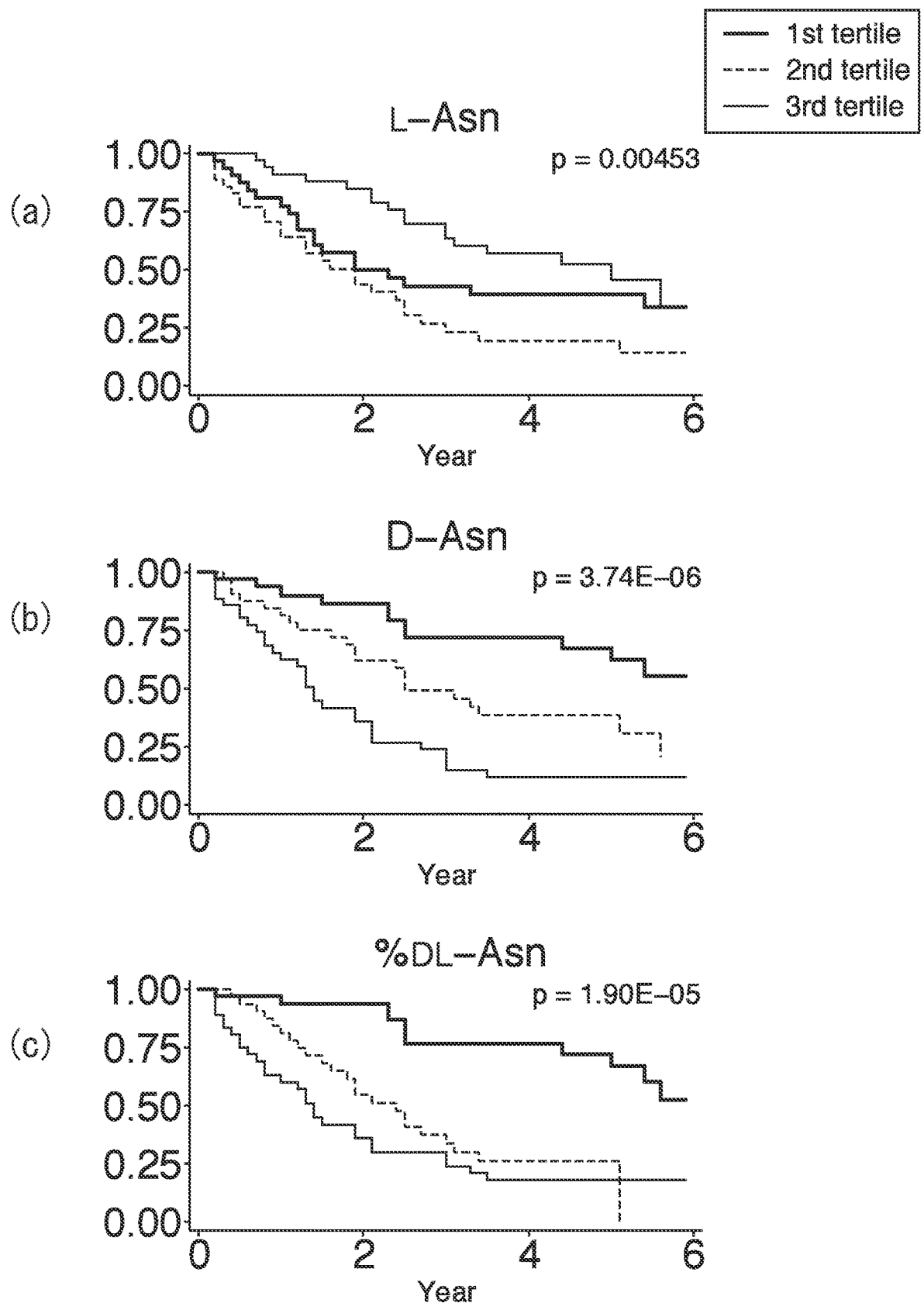
FIG. 1 indicates the results of dividing (a) amount of L-asparagine, (b) amount of D-asparagine and (c) ratio of D-asparagine/L-asparagine at baseline into three tertiles among cohorts including 108 kidney disease patients and subjecting prognosis thereof to a Kaplan-Meier analysis.

The method for predicting a prognosis for kidney disease according to the present invention includes a step for measuring the amount at least one chiral amino acid in a blood sample of a subject, and a steps for correlating the measured amount of that chiral amino acid with the prognosis for the subject.

The step for measuring the amount of chiral amino acid can be measuring the amount of a target amino acid only or collectively measuring other chiral amino acids. Since chiral amino acids can also serve as markers for diseases other than kidney disease, the D-forms and L-forms of twenty types of proteinogenic amino acids present in a blood sample are preferably measured collectively from the viewpoint of analyzing a plurality of diseases all at once. A step for acquiring the blood sample and a step for treating the acquired blood sample may be carried out prior to the step for measuring the amount of chiral amino acid.

The step for correlating the measured amount of chiral amino acid with a prognosis for the subject may use any arbitrary technique provided a correlation can be made with a prognosis for the subject using the measured amount of chiral amino acid. Correlation may be carried out using only the measured amount of chiral amino acid or correlation may be carried out with an index value that is resulted from processing the measured amount of chiral amino acid with an arbitrary variable or constant. In the present invention, an index value may be the measured amount of an amino acid, may be calculated based on a measured amount, or may be, for example, the concentration ratio or percentage, and the like against a corresponding isomer (such as f L-form in the case of D-form, D-form in the case of L-form). In addition to the amount of the corresponding isomer, any arbitrary variable having an influence on the amount of chiral amino acid can be used as a variable, such as age, body weight, gender, BMI or eGFR.

The step for correlating with the prognosis for a subject can be carried out by correlating with a poor prognosis for kidney disease in the case the amount of a specific chiral amino acid has exceeded a cutoff value, or by correlating with a favorable prognosis for kidney disease in the case the amount of a specific chiral amino acid does not exceed a cutoff value. Whether a cutoff value is exceeded on the high side or low side can be suitably selected corresponding whether the chiral amino acid used increases or decreases in the case of suffering from kidney disease. For example, since D-amino acids increases in kidney disease patients, a specific D-amino acid is correlated with a poor prognosis for kidney disease in the case of belonging to a high level group or is correlated with a favorable prognosis for kidney disease in the case of belonging to a low level group. In order to determine whether or not belonging to a high group, a step for comparing with a predetermined cutoff value may be included, and an assessment step for assessing prognosis based on the result of that comparison may be further included.

Although prognosis refers to the medical outlook regarding the course followed by a disease in the case of having become afflicted with that disease, in the present invention, the outlook regarding the course followed by a disease can be predicted for subjects not afflicted with a disease or for whom affliction with a disease has not been determined. Thus, a subject in the present invention includes a kidney disease patient, subject not yet diagnosed with kidney disease and healthy individuals. Patients suffering from a disease other than kidney disease may also be included in these subjects.

Prediction of a prognosis for kidney disease can also be said to be a classification or stratification of the risk for kidney disease in the future. Although there are no particular limitations thereon, examples of a poor prognosis as predicted by prognosis prediction include kidney outcome, or in other words, end-stage kidney disease (ESKD) and death. All causes of death may be included in death or, more preferably, only those causes of death that correlate with kidney disease. End-stage kidney disease (ESKD) refers to the terminal state of chronic kidney disease and is a state requiring renal replacement therapy such as dialysis or kidney transplant. Prognosis prediction of the present invention makes it possible to determine the need for renal replacement therapy or the potential for death of a subject at some point in the future regardless of the current disease status of that subject. The point in time for which prognosis is predicted may be any arbitrary point in time, and can be arbitrarily selected corresponding to the cohorts used and study period. Any arbitrary point in time can be selected from groups consisting of, for example, 3 months, 6 months, 1 year, 2 years, 3 years, 4 years, 5 years, 6 years and 10 years in the future.

More specifically, prognosis prediction makes it possible classify the amount of at least one chiral amino acid present in a blood sample into two or more groups followed by predicting prognosis corresponding to that classification. Since the present inventors found that, prognosis for kidney disease is poor if the amount of a D-amino acid among chiral amino acids present in the blood becomes high, a subject can be correlated with a poor prognosis in the case of belonging to a high level group, thereby making it possible to predict or assess prognosis as a result thereof. Thus, the method for predicting prognosis may be carried out by medical assistant who is not a physician or can be carried out by an analysis laboratory and the like. Thus, the method for predicting prognosis of the present invention can be said to be a preliminary or auxiliary method for making a diagnosis.

The borderline of a high level group can be arbitrarily determined by analyzing and statistically processing cohorts. A method commonly known among persons with ordinary skill in the art may be used for the statistical processing method, and examples of methods used include Kaplan-Meier analysis and the Cox proportional hazards model. Although the cutoff value used to determine the borderline varies according to the type of cohorts, examples of cutoff values that can be used include of a value of 5.6 µmol/L for D-serine, 0.7 µmol/L for D-asparagine, 4.7 µmol/L for D-proline, 5.2 µmol/L for D-alanine, 0.5 µmol/L for D-leucine, 0.6 µmol/L for D-lysine, 0.1 µmol/L for D-alloisoleucine, 65.0 µmol/L for L-glutamic acid, 460 µmol/L for L-alanine, 42.4 µmol/L for L-tryptophan, 67.2 µmol/L for L-asparagine and 32 µmol/L for L-aspartic acid as determined by Kaplan-Meier analysis of cohorts used in examples of the present application. In addition, since D-allo-isoleucine, D-leucine and D-lysine are observed in patients reaching kidney outcome (end-stage kidney disease requiring renal replacement therapy and death by any cause), while these are hardly observed at all in subjects not reaching kidney outcome, if these chiral amino acids are present at a level equal to or greater than the limit of detection, that subject can be assessed as having a poor prognosis. In the case D-amino acid concentration in the blood of a subject is higher than these cutoff values, there is a high likelihood of that subject entering end-stage kidney disease (ESKD) or dying at some point in the future, and can be assessed as having a poor prognosis. However, this is not intended to limit the cutoff value used to the aforementioned cutoff values.

In the present invention, a specific chiral amino acid refers to the D-form or L-form of a proteinogenic amino acid. Although internal kinetics and metabolism vary between D-forms and L-forms, distinguish between the D-form and L-form make it possible to predict prognosis with high accuracy. Examples of proteinogenic amino acids include alanine (Ala), arginine (Arg), asparagine (Asn), aspartic acid (Asp), cysteine (Cys), glutamine (Gin), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Among these, D-serine (D-Ser), D-asparagine (D-Asn), D-alanine (D-Ala), D-proline (D-pro), D-leucine (D-Leu), D-lysine (D-Lys), D-alloisoleucine (D-allo-Ile), L-glutamic acid (L-Glu), L-alanine (L-Ala), L-tryptophan (L-Trp), L-asparagine (L-Asn) and L-aspartic acid (L-Asp) are preferable from the viewpoint of enabling more accurate prediction of prognosis. D-serine (D-Ser), D-asparagine (D-Asn), D-alanine (D-Ala), D-proline (D-Pro), D-leucine (D-Leu), D-lysine (D-Lys) and D-allo-isoleucine (D-allo-Ile) are more preferably from the viewpoint of enabling more accurate prediction of prognosis. D-serine (D-Ser) is even more preferable from the viewpoint of enabling even more accurate prediction of prognosis.

Measurement of the amount of chiral amino acids in a sample may be carried out using any method commonly known among persons with ordinary skill in the art.

For example, the D-form and L-form of an amino acid can be measured simultaneously by a method consisting of preliminarily specifically derivatizing D- and L-amino acids in a stereoisomeric manner with o-phthalaldehyde (OPA), N-tert-butyloxycarbonyl-L-cysteine (Boc-L-Cys) or other modifying reagent followed by separating by means of an analysis column, such as ODS-80TsQA column, with using a mixture of 100 mM acetate buffer (pH 6.0) and acetonitrile for gradient elution. In addition, a method consisting of preliminarily derivatizing D- and L-amino acids with a fluorescent reagent, such as 4-fluoro-7-nitro-2,1,3-benzoxazole (NBD-F) followed by specifically separating each amino acid in non-stereoisomeric manner by means of an analysis column, such as ODS-80TsQA, Mightysil RP-18GP column, etc., and then optically resolving using a Pirkle-type chiral stationary phase column (such as the Sumichiral OA-2500S or OA-2500R), can be used to measure trace amounts of proteinogenic amino acids (Hamase, K. and Zaitsu, K., Analytical Chemistry, Vol. 53, 677-690 (2004)). An optical resolution column system in the present description refers to a separation and analysis system that at least uses an optical resolution column, and may include separation and analysis by an analysis column other than an optical resolution column. More specifically, the concentrations of D- and L-amino acids in a sample can be measured by using a method for analyzing optical isomers characterized in comprising a step for passing a sample containing a component having optical isomers through a first column filler serving as a stationary phase together with a first liquid as a mobile phase to separate the components in the sample, a step for individually retaining each of the components of the sample in a multi-loop unit, a step for supplying each of the components of the sample retained in the multi-loop unit to a second column filler having an optically active center serving as a stationary phase together with a second liquid serving as a mobile phase to separate the optical isomers contained in each of the components of the sample through a flow path, and a step for detecting the optical isomers contained in each of the components of the sample (Japanese Patent No. 4291628). Alternatively, D-amino acids can be assayed by an immunological method using monoclonal antibody capable of identifying optical isomers of amino acids, such as monoclonal antibody that specifically binds with D-leucine or D-aspartic acid and the like (Japanese Unexamined Patent Publication No. 2009-184981).

In the present invention, an index value based on a chiral amino acid in a blood sample may be used alone to predict prognosis, or can be used to predict prognosis by combining with an index value based on the amounts of one or more other chiral amino acids capable of being used to predict prognosis. In addition, the method for predicting prognosis of the present invention may also further include a step for measuring a variable relating to kidney disease, and can be correlated with prognosis by combining an index value based on the amount of a chiral amino acid with that variable. Examples of such variables include history of diabetes, age, gender, hemoglobin level, mean blood pressure, history of cardiovascular events and the use or non-use of anti-hypertensive drugs, as well as known kidney disease diagnostic or prognosis predictive markers. Examples of such known kidney disease diagnostic or prognosis predictive markers include eGFR, blood creatinine concentration, cystatin C and urinary protein level. These variables are taken into consideration on the basis of established methods for statistical processing. For example, variables can be taken into consideration in a multiple Cox regression analysis using, for example, STATA Statistical Software Version 11 (STATA Corp., College Station, Tex., USA).

In the case of predicting or assessing a prognosis using the method for predicting a prognosis of the present invention, treatment is further carried out corresponding to that prognosis. Although not limited thereto, in the case a poor prognosis has been predicted or assessed, it is necessary to further carry out treatment such as lifestyle improvement, dietary counseling, blood pressure management, blood sugar management or lipid management. Quitting smoking or exercise for lowering BMI, for example, is recommended for lifestyle improvement. Reduction of salt intake for the purpose of improving hypertension is recommended for dietary counseling. Administration of an ACE inhibitor or ARB for the purpose of improving hypertension is recommended for blood pressure management. Administration of insulin for the purpose of lowering HbA1c is recommended for blood sugar management. Administration of hyperlipidemia drugs for the purpose of lowering LDL cholesterol levels is recommended for lipid management. These treatment strategies are determined after having been discussed with a physician based on the amounts of chiral amino acids. Thus, in another aspect thereof, the present invention relates to a method for treating kidney disease that includes carrying out the method for predicting a prognosis of the present invention and then further carrying out treatment of that kidney disease.

Assessment of kidney disease is carried out based on the amount of at least one chiral amino acid present in a blood sample.

Since the inventors of the present invention found that there is a correlation between the amounts of at least one chiral amino acid in the blood selected from the group consisting of D-asparagine, D-serine, D-aspartic acid, D-allothreonine, D-alanine, D-proline, D-leucine, L-histidine, L-serine, L-aspartic acid, L-alanine, L-isoleucine, L-phenylalanine, L-tryptophan, L-lysine and L-tyrosine and eGFR values (FIGS. 4A to L), kidney disease can be identified using the amounts of these chiral amino acids. More specifically, kidney disease can be assessed by applying the amount of at least one chiral amino acid present in a blood sample to two or more pre-classified groups, and in still another aspect, the severity of kidney disease can also be assessed.

The borderline for assessing kidney disease can also be arbitrarily determined by similarly analyzing cohorts and performing statistical processing. A method commonly known among persons with ordinary skill in the art may be used for the statistical processing method, examples of which include ROC analysis and the t-test, or the mean, median and X percentile values of a healthy subject group or patient group can be used. Here, an arbitrary value can be selected for X, and a value of 3, 5, 10, 15, 20, 30, 40, 60, 70, 80, 85, 90, 95 or 97 can be suitably used. The cutoff value may consist of a single cutoff value or pathology may be classified according to the severity of the disease. Examples of chiral amino acids used to assess kidney disease include D-asparagine, D-serine, D-aspartic acid, D-allo-threonine, D-alanine, D-proline, D-leucine, L-histidine, L-serine, L-aspartic acid, L-alanine, L-isoleucine, L-phenylalanine, L-tryptophan, L-lysine and L-tyrosine. The cutoff value of each can be arbitrarily determined by carrying out a cohort analysis. A subject is assessed as having kidney disease in the case the D-amino acid concentration in the blood of the subject is higher than the cutoff value.

In still another aspect of the present invention, the present invention relates to a method for determining eGFR values based on the amount of at least one chiral amino acid in a blood sample. This method includes a step for measuring the amount of at least one chiral amino acid in a blood sample and a step for determining an eGFR value based on the measured value of that at least one chiral amino acid. In one aspect thereof, the step for determining an eGFR value based on the measured value of a chiral amino acid is able to determine the amount thereof based on a predetermined regression curve. In still another aspect, the step for determining an eGFR value based on the measured amount of a chiral amino acid consists of preliminarily dividing cohorts into a plurality of groups corresponding to the amount of a chiral amino acid, correlating the groups with eGFR values or a range thereof, and classifying the measured values for the groups. At least one chiral amino acid selected from the group consisting of D-asparagine, D-serine, D-aspartic acid, D-allothreonine, D-alanine, D-proline, D-leucine, L-histidine, L-serine, L-aspartic acid, L-alanine, L-isoleucine, L-phenylalanine, L-tryptophan, L-lysine and L-tyrosine can be used for the chiral amino acid.

Figure 14:
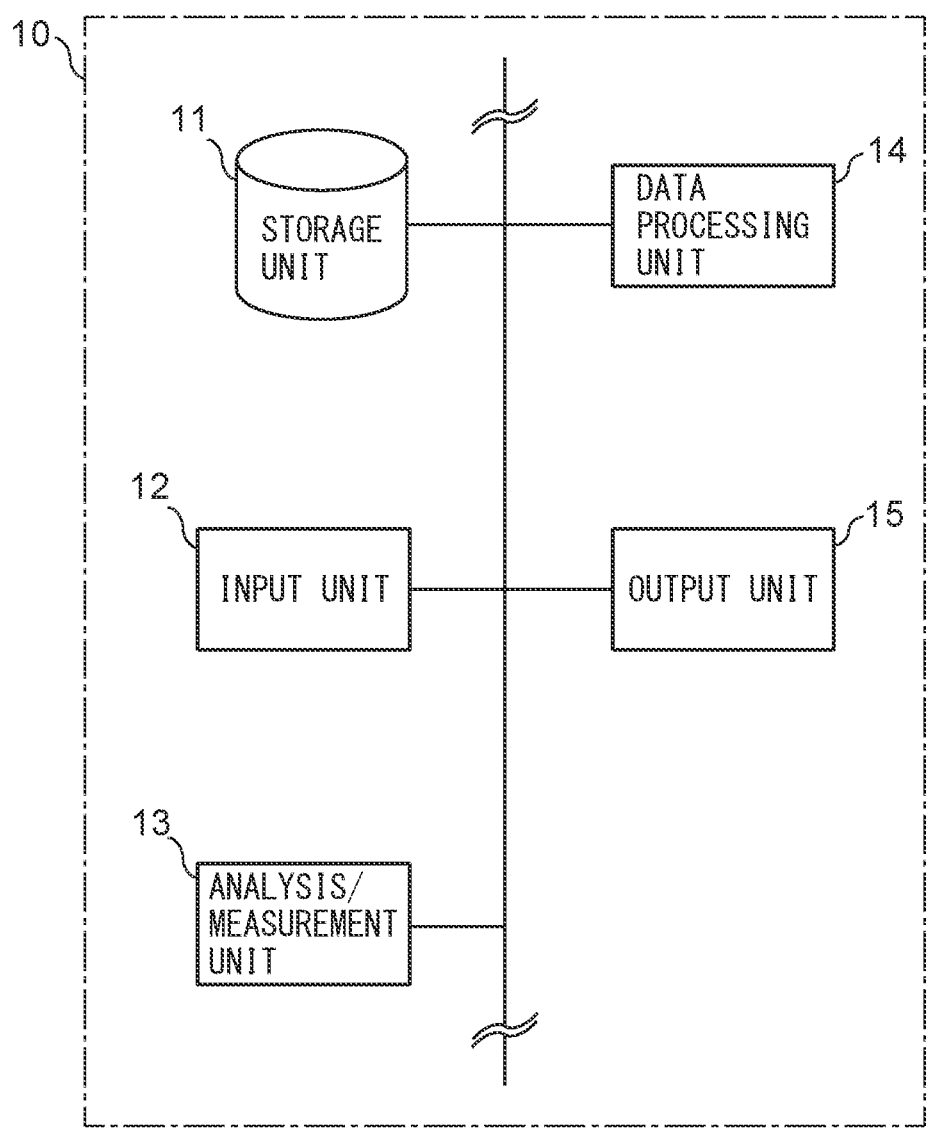
FIG. 14 is a block diagram of the prognosis prediction analysis system of the present invention.

The sample analysis system and program of the present invention is composed so as to carry out the prognosis prediction method of the present invention. FIG. 14 is a block diagram of the sample analysis system of the present invention. This sample analysis system 10 comprises a storage unit 11, an input unit 12, an analysis/measurement unit 13, a data processing unit 14 and an output unit 15, and is able to analyze a blood sample and output prognosis information. More specifically, in the sample analysis system 10 of the present invention, the storage unit 11 stores a cutoff value of an index value based on the amount of a chiral amino acid in the blood for determining a prognosis for a kidney disease and the prognosis information, which are input from the input unit 12 the analysis/measurement unit 13 separates at least one chiral amino acid among the proteinogenic amino acids present in the blood sample of the subject and assays the amount of that chiral amino acid, the data processing unit 14 calculates an index value based on the measured amount of the at least one chiral amino acid and compares that index value with the cutoff value stored in the storage unit 11 to determine prognosis information of the target kidney disease, and the output unit 15 is able to output pathology information based on the prognosis for the target kidney disease.

The storage unit 11 has a memory device such as RAM, ROM or flash memory, a stationary disk device such as a hard disk drive, or a portable storage device such as a flexible disk or optic disk. The storage unit stores data measured with the analysis/measurement unit, data and instructions input from the input unit, the results of arithmetic processing performed with the data processing unit, as well as a computer program, database and the like used for various types of processing by an information processing device. The computer program may be installed via a computer-readable storage medium such as a CD-ROM or DVD-ROM or by accessing from the Internet. The computer program is installed in the storage unit using a known setup program and the like.

The input unit 12 functions as an interface and the like and contains an operating unit such as a keyboard or mouse. The input unit is able to input data measured with the analysis/measurement unit 13 and instructions and the like for arithmetic processing performed with the data processing unit 14. When the analysis/measurement unit 13 is present outside, in addition to the operating unit, the input unit 12 may also contain an interface and the like that enables input of measured data and the like via a network or storage medium.

The analysis/measurement unit 13 carries out the step for measuring the amount of a chiral amino acid in a blood sample. Thus, the analysis/measurement unit 13 has a configuration that enables separation and measurement of chiral amino acids. Although one amino acid may be analyzed at a time, some or all types of amino acids can be analyzed collectively. Without intending to limit to that indicated below, the analysis/measurement unit 13 may be a high-performance liquid chromatography (HPLC) system comprising, for example, a sample introduction unit, optical resolution column and detection unit. The analysis/measurement unit 13 may be composed separate from the sample analysis system or measured data and the like may be input via the input unit 12 using a network or storage medium.

The data processing unit 14 is composed so as to determine a prognosis of kidney disease by calculating an index value from the measured amount of a measured chiral amino acid and comparing the resulting index value with a cutoff value stored in the storage unit 11. The data processing unit 14 performs various types of arithmetic processing on data measured with the analysis/measurement unit 13 and stored in the storage unit 11 in accordance with a program stored in the storage unit. Arithmetic processing is carried out by a CPU contained in the data processing unit. This CPU contains a functional module that controls the analysis/measurement unit 13, input unit 12, storage unit 11 and output unit 15, and is able to carry out various types of control. Each of these units may be respectively and independently controlled with integrated circuits, microprocessors or firmware and the like.

The output unit 15 is composed so as to output results obtained by arithmetic processing with the data processing unit in the form of pathology index values and/or pathology information. The output unit 15 may be an output means such as a printer or display device such as a liquid crystal display that directly displays the results of arithmetic processing or an output, or may be an interface unit for output to an external storage device or output via a network.

Figure 15:
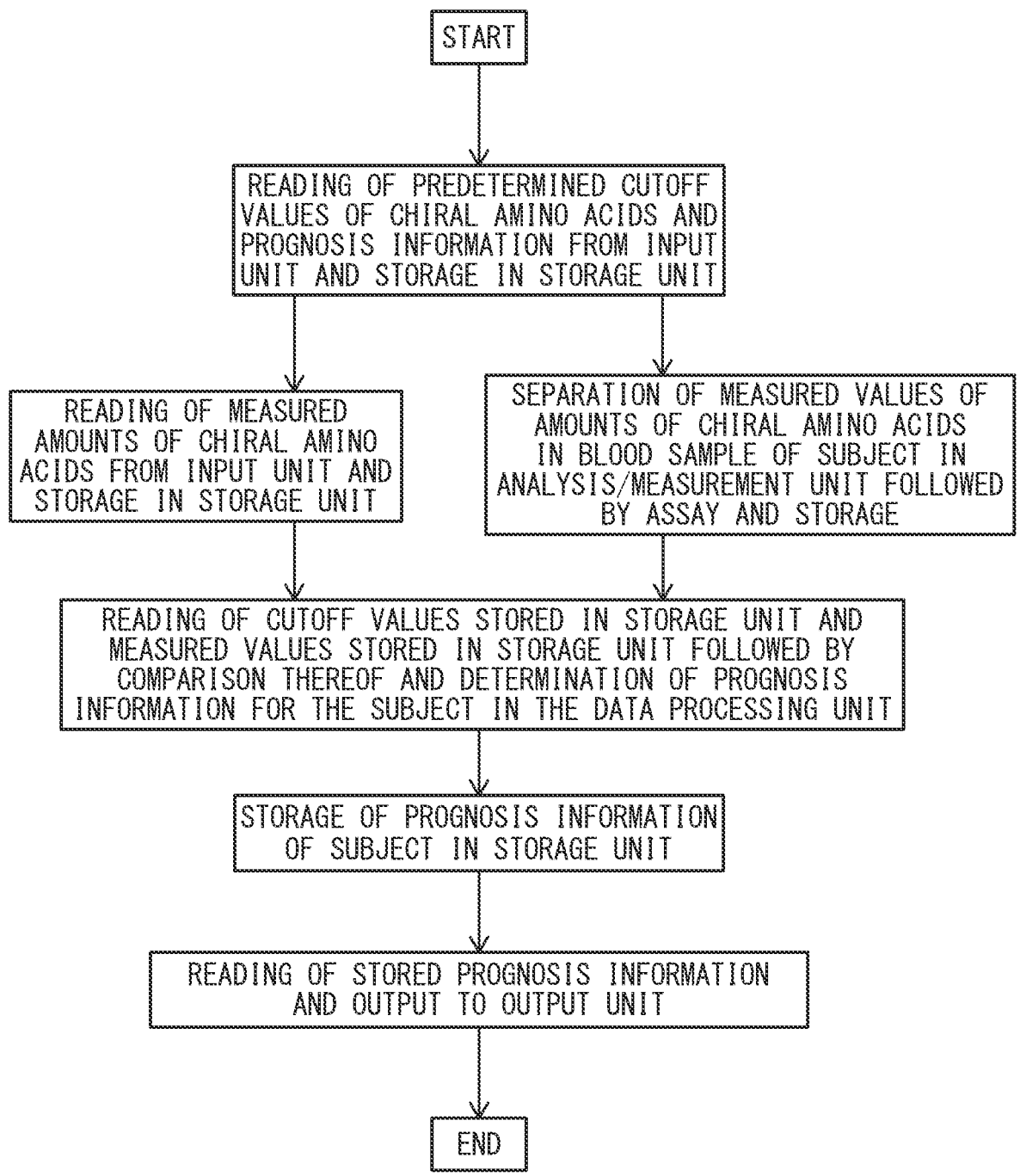
FIG. 15 is a flow chart indicating an example of an operation for determining a prognosis for kidney disease.

FIG. 15 is a flow chart indicating an example of an operation for determining a prognosis according to the program of the present invention, and FIG. 15 is a flow chart indicating an example of an operation for determining prognosis information according to the program of the present invention.

More specifically, the program of the present invention is a program letting a data processing device comprising an input unit, an output unit, a data processing unit and a storage unit to determine prognosis information. The program of the present invention comprising commands to be executed by the aforementioned information processing device:

for storing prognosis information and cutoff values of predetermined index values of at least one chiral amino acid which are input from the input unit, for the storage unit storing measured values of the amount of at least one chiral amino acid which are input from the input unit, for the storage unit calculating index values in the data processing unit based on measured values stored in the storage unit and comparing the index values with cutoff values stored to determine prognosis information, for the storage unit storing the prognosis information, and for the output unit outputting the stored prognosis information. The program of the present invention may be housed in a storage medium or may be provided via a telecommunication line such as the Internet or LAN.

In another aspect of the present invention, the present invention relates to a system for determining eGFR values that carries out the method for determining eGFR values of the present invention. This system comprises a storage unit, an input unit, a data processing unit and an output unit, and carries out the following step:

inputting the amounts of at least type of one amino acid among chiral amino acids present in the blood for determining eGFR values and a regression curve or cutoff values of those eGFR values from the input unit and storing them in the storage unit, inputting the measured values of the amount of at least one type of amino acid among chiral amino acids present in a blood sample of a subject from the input unit, and storing them in the storage unit, having the data processing unit to determine the eGFR value of the subject based on the stored measured value of the amount of the aforementioned amino acid and the aforementioned regression curve or cutoff value, and outputting eGFR value to the output unit.

In the case the data processing device is provided with an analysis/measurement unit, instead of inputting values of the amounts of at least one chiral amino acid from the input unit, the analysis/measurement unit may contain commands for having the information processing device execute separation and measurement of chiral amino acids from a blood sample and storage of the measured values in the storage unit.

All documents mentioned in the present description are incorporated in their entirety herein by reference.

Examples of the present invention as explained below are indicated for the purpose of exemplification only, and do not limit the technical scope of the present invention. The technical scope of the present invention is only limited by the scope of claim for patent. The present invention can be modified, such as by adding, deleting or substituting constituents of the present invention, on the condition that such modification does not deviate from the gist of the present invention.

Examples

Group and Sample Analysis

The inventors of the present invention registered 118 consecutive patients suffering from stage 3, 4 and 5 CKD, who were not undergoing dialysis, from the First Department of Nephrology of the Rinku General Medical Center in a prospective study from August in 2005 to January in 2009. After fasting overnight, baseline blood sample were collected from the patients and plasma was prepared by placing in plastic tubes. Patients from whom inadequate blood samples were unable to be acquired were omitted in advance.

The study was approved by the ethics committee of the Rinku General Medical Center and was conducted on the basis of the Declaration of Helsinki.

Baseline inclusion criteria consisted of age of less than 90 years, absence of complications associated with malignant tumor and absence of infection. Patients from whom complete baseline data was unable to be acquired (n=2) or patients from whom adequate blood samples were unable to be acquired (n=4), and patients who began renal replacement therapy within 1 month after registration (n=4) were omitted from the study. The study was approved by the institutional ethics committee of the Rinku General Medical Center and the Osaka City General Hospital, and written informed consent to participate in the study was obtained from all patients. Renal function was evaluated from baseline data obtained during initial examination at this facility using estimated glomerular filtration rate (eGFR) based on an equation newly developed for Japanese.

That equation is as follows:

$$eGFR = 194 \times serum\ creatinine\ (SCr)^{-1.094} \times age^{-0.287} \quad [\text{Math. 1}]$$

(wherein, the units for age are years, the units for SCr are mg/dL, and the units for estimated glomerular filtration rate (eGFR) are mL/min/body surface area of 1.73 m$^2$).

A correction factor of 0.739 was multiplied by the value calculated from the formula for female patients.

Serum creatinine was measured by an in-house enzymatic method. Random urine samples (10 ml) were collected at the time of baseline determination followed by measurement of the ratios of urinary protein and creatinine. Other variables used when determining the baseline consisted of age, gender, diabetes as defined according to codes E10 to E14 of the 10th edition of the International Classification of Diseases (ICD), systolic blood pressure, diastolic blood pressure, hemoglobin level and the use of renin-angiotensin system inhibitors, β-blockers and calcium blockers. Baseline characteristics of the patients were as indicated below.

TABLE 1

Patient Baseline Characteristics

| Characteristic | All Patients(n = 108) |
|---|---|
| Age (years) | 65.3 ± 10.9 |
| Proportion of males (%) | 75.0 |
| eGFR (mL/min/1.73 m$^2$) | 21.0 ± 12.4 |
| Mean blood pressure (mmHg) | 95.1 ± 12.9 |
| Systolic blood pressure | 139.1 ± 21.7 |
| Diastolic blood pressure | 73.2 ± 11.7 |
| Hemoglobin (g/dL) | 11.0 ± 1.9 |
| Urinary protein (g/gCre) | 2.8 ± 3.8 |
| Patient origin(%) | |
| Diabetes | 30.6 |
| Chronic glomerulonephritis | 23.1 |
| Benign glomerulosclerosis | 35.2 |
| Other | 10.2 |
| Use of ACEi and/or ARB (%) | 68.8 |
| Use of β-blockers (%) | 32.4 |
| Use of calcium blockers (%) | 67.6 |

Values are indicated as the mean±SD or as percent (%).

eGFR: Estimated glomerular filtration rate, ACEi: Angiotensin-converting enzyme inhibitor, ARB: Angiotensin II receptor blocker In the present study, the initial endpoint defined as kidney outcome was the total of end-stage kidney disease (ESKD) requiring renal replacement therapy and all deaths. The patients underwent routine follow-up care on an outpatient basis. The data was gathered in the form of a source document in the end of 2011. Baseline and follow-up data were collected from hospital medical records and discharge summaries, outpatient records, interviews conducted at the time of initial examination and with the physician in charge of dialysis care, and death certificates. Endpoint was confirmed by at least two physicians. Patient follow-up data was able to be used accurately. This is because (i) this facility is a central hospital located in the southern part of Osaka prefecture and there are no other central hospitals located in this area, and (ii) there is a favorable working relationship with local physicians responsible for the initial examination and dialysis care.

Sample Preparation

Preparation of samples from human plasma was carried out in accordance with a modification of the procedure described in the Journal of Chromatography. B, Analytical technologies in the biomedical and life science, 966, 187-192 (2014). In short, this procedure consists of adding 20 volumes of methanol to the plasma, transferring a fixed amount (10 µl of supernatant obtained from the methanol homogenate) to a brown tube, and derivatizing with NBD (using 0.5 µl of plasma in the reaction). The solution is then dried under reduced pressure followed by the addition of 20 µl of 200 mM sodium borate buffer (pH 8.0) and 5 µl of a fluorescent labeling reagent (anhydrous MeCN containing 40 mM 4-fluoro-7-nitro-2,1,3-benzoxazole (NBD-F)) and heating for 2 minutes at 60° C. 0.1% aqueous TFA solution (75 µl) is then added and 2 µl of this reaction mixture is used in 2D-HPLC.

Measurement of Amino Acid Enantiomers by 2D-HPLC

Amino acid enantiomers were assayed using a Micro 2D-HPLC platform as described in J. Chromatogr. A: 1217, 1056-1062 (2010) and the Journal of Chromatography, B: Analytical technologies in the biomedical and life sciences, 877, 2506-2512 (2009). In short, NBD derivatives of the amino acids were eluted by gradient elution using an aqueous mobile phase containing MeCN, THF and TFA using a reverse phase column (Monolithic ODS Column, 0.53 mm i.d.×100 mm, Shiseido Japan Co., Ltd.). Target amino acid fractions were recovered automatically using a multi-loop valve in order to separate and measure the D- and L-forms followed by supplying to an enantiomer selection column (KSAACSP-001S or Sumichiral oA-3200, 1.5 mm i.d.×250 mm, self-filling, materials acquired from Shiseido Japan and Sumika Chemical Analysis Services). In the case of measuring Ile and Thr having four types of stereoisomers, the L- and D-forms along with diastereoisomers (L-allo form and D-allo form) were separated by the first dimensional reverse phase mode (and these diastereoisomers are separated in the reverse phase mode). Next, the enantiomers (L- and D-forms and L-allo- and D-allo forms) were separated two-dimensionally with an enantiomer selection column. The mobile phase consisted of a mixed solution of MeOH and MeCN containing citric acid or formic acid, and fluorescence of the NBD-amino acids was excited at 470 nm and detected at 530 nm. All assay data was acquired by fluorescence detection. The actual presence of D-amino acids in the biological matrix was confirmed using HPLC-MS/MS.

Statistical Processing

Continuous variables were indicated as the range of a median value or as an interquartile range (IQR). Discrete data was given as a count and ratio (%). Metabolites were indicated as a median value (quartile). Correlations were evaluated using Spearman rank regression analysis. The diagnosis role of metabolites was evaluated by generating a plurality of Cox proportional hazards models and adjusting with the baseline characteristics. A statistically significant difference was defined as P<0.05. Statistical analysis was carried out using STATA Statistical Software Version 11 (STATA Corp., College Station, Tex., USA).

Results

Cohort Amino Acid Metabolomic Profiles

The inventors of the present invention carried out chiral amino acid metabolomic profiling on long-term cohorts composed of CKD patients. Data was generated from 108 participants having a median value of the follow-up period of 4.3 years (interquartile range: 2.4 years to 5.5 years). None of patients withdrew from follow-up. Baseline characteristics are shown in Table 1. Among these patients, 58 began renal replacement therapy and 15 died, with 4 of the 15 patients dying prior to the start of renal replacement therapy. Chiral amino acid metabolomic profiling was carried on these cohorts using the two-dimensional HPLC. This system makes it possible to detect enantiomers of proteinogenic amino acids over a range of about 1 fmol to 1 pmol based on chiral selectivity without being affected by significant interference from intrinsic substances. The relative standard deviation over the study period (n=4) was 1.10% to 8.19%. Analyses were carried out twice using several samples in consideration of reproducibility when analyzing human plasma samples, and nearly the same results were obtained. The plasma of CKD patients was observed. D-Ser, D-Ala, D-Pro and D-Asn were detected in many of the patients (89% to 100%), D-Asp, D-Lys, D-Allothr, D-Glu, D-Arg and D-His were detected in 10% to 40% of the patients, and D-Leu, D-Phe and D-AlloIle were only sporadically detected (detected in less than 10% of the patients). It should be noted that the AlloThr detected in these cohorts consisted of D-AlloThr only. In the body, conversion of α-carbon occurs primarily and D-allo forms are formed from L-Thr and L-Ile. As a result, the amount of the D-allo form is greater than the D-forms of these two amino acids.

Correlation Between Chiral Amino Acids and Clinical Parameters

The inventors of the present invention evaluated the baseline correlation between clinical parameters and chiral amino acids. The levels of D-Ser, D-Pro and D-Asn demonstrated an inverse correlation with estimated glomerular filtration rate (eGFR). On the other hand, other amino acids consisting of D-Ala, D-Asp and D-AlloThr only demonstrated weak correlations. It is interesting to note that the level of L-Ser demonstrated a positive correlation with eGFR, and thus D/L-Ser demonstrated an even stronger correlation with eGFR (FIGS. 16A to 16L).

Correlation Between Kidney Outcome and Chiral Amino Acids

Figure 2:
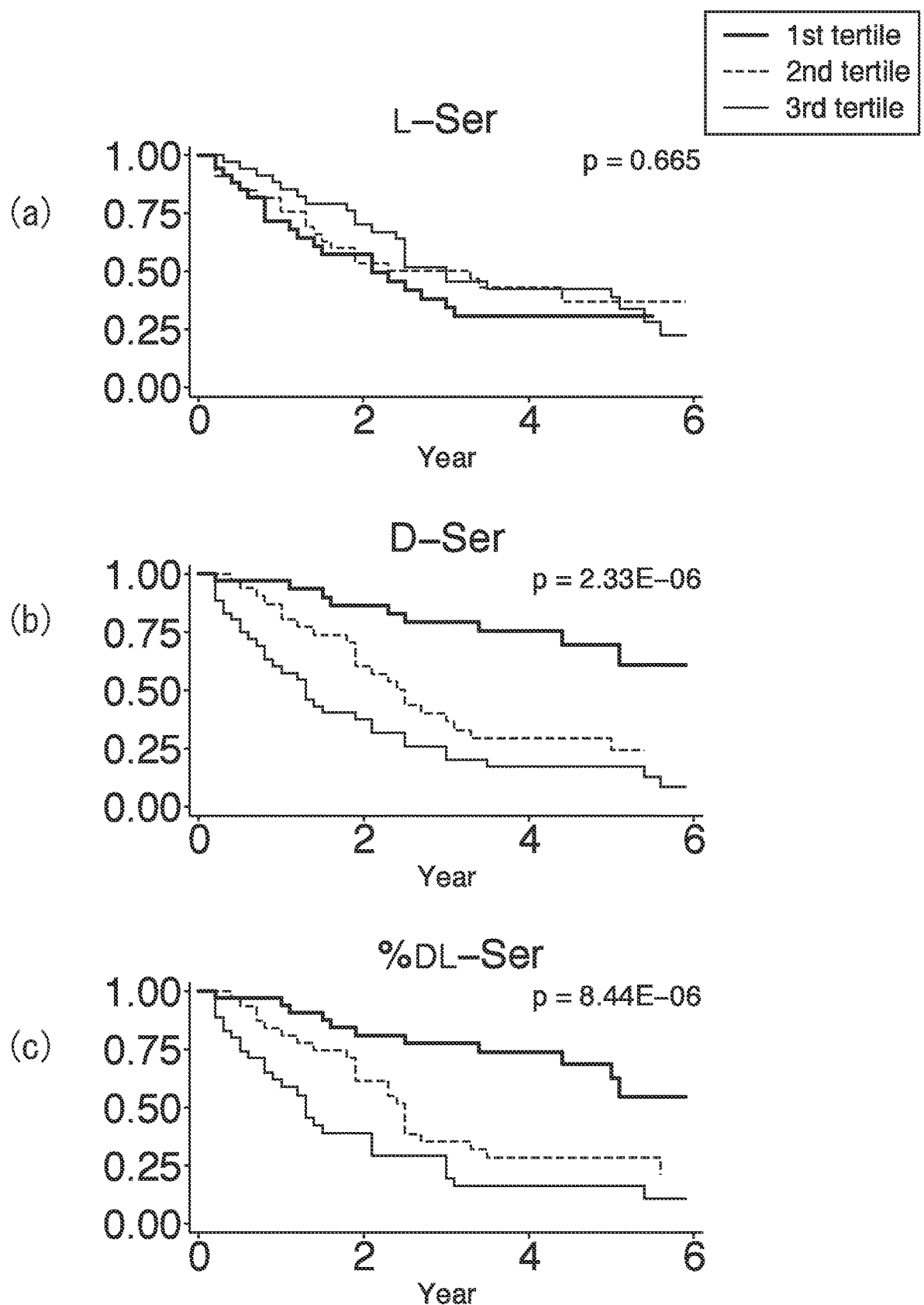
FIG. 2 indicates the results of dividing (a) amount of L-serine, (b) amount of D-serine and (c) ratio of D-serine/L-serine at baseline into three tertiles among cohorts including 108 kidney disease patients and subjecting prognoses thereof to a Kaplan-Meier analysis.
Figure 3:
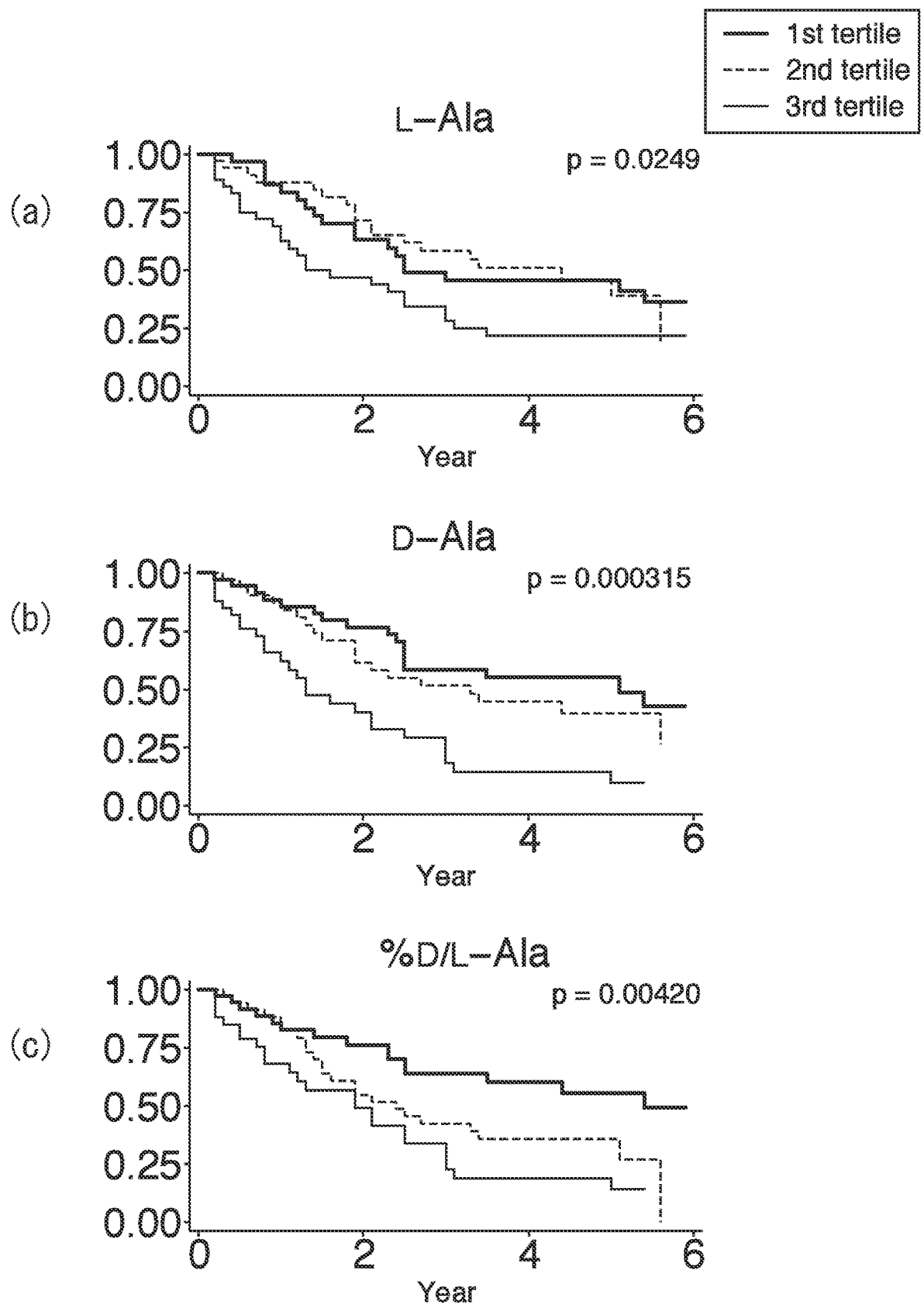
FIG. 3 indicates the results of dividing (a) amount of L-alanine, (b) amount of D-alanine and (c) ratio of D-alanine/L-alanine at baseline into three tertiles among cohorts including 108 kidney disease patients and subjecting prognoses thereof to a Kaplan-Meier analysis.
Figure 4:
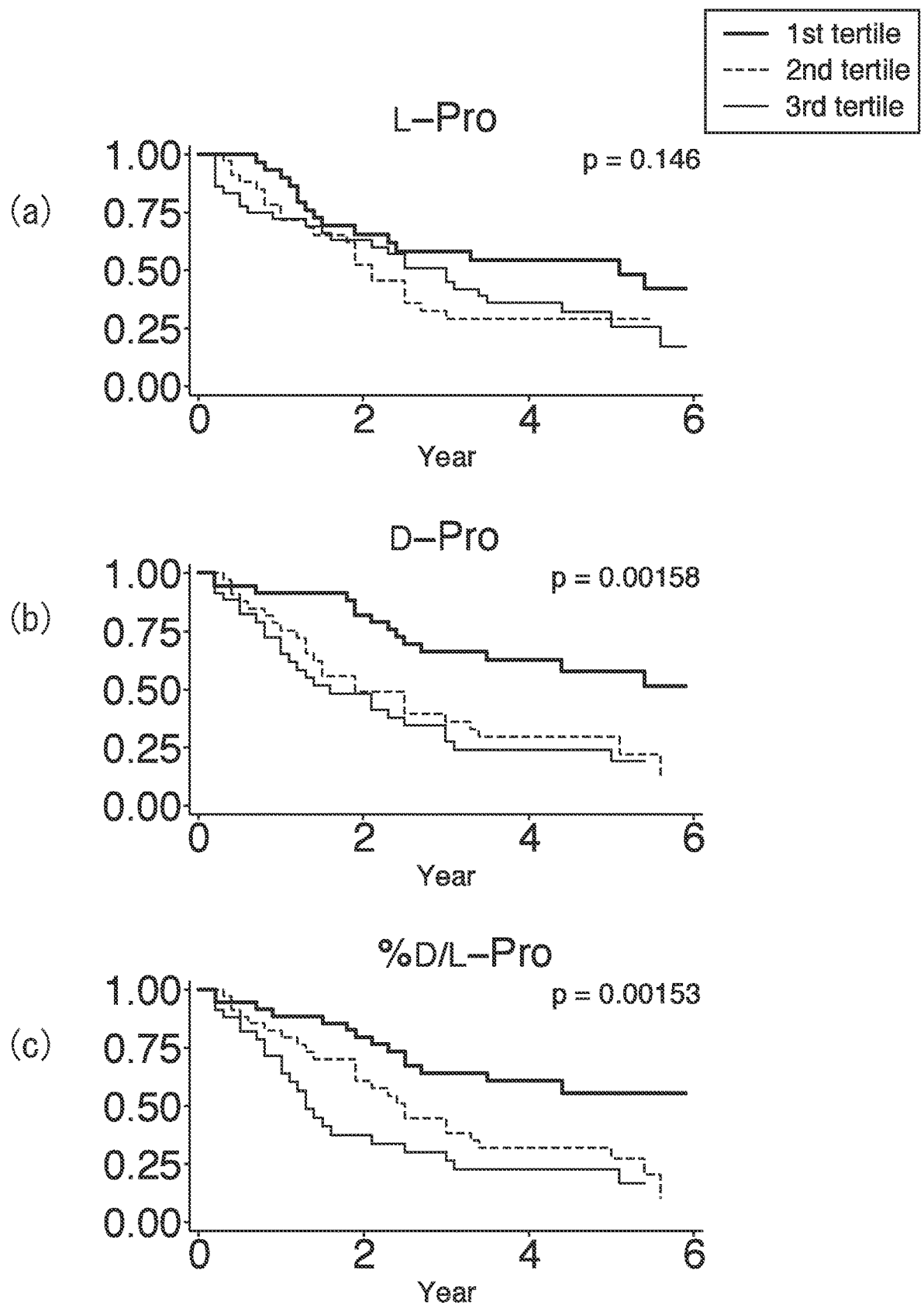
FIG. 4 indicates the results of dividing (a) amount of L-proline, (b) amount of D-proline and (c) ratio of D-proline/L-proline at baseline into three tertiles among cohorts including 108 kidney disease patients and subjecting prognoses thereof to a Kaplan-Meier analysis.
Figure 5:
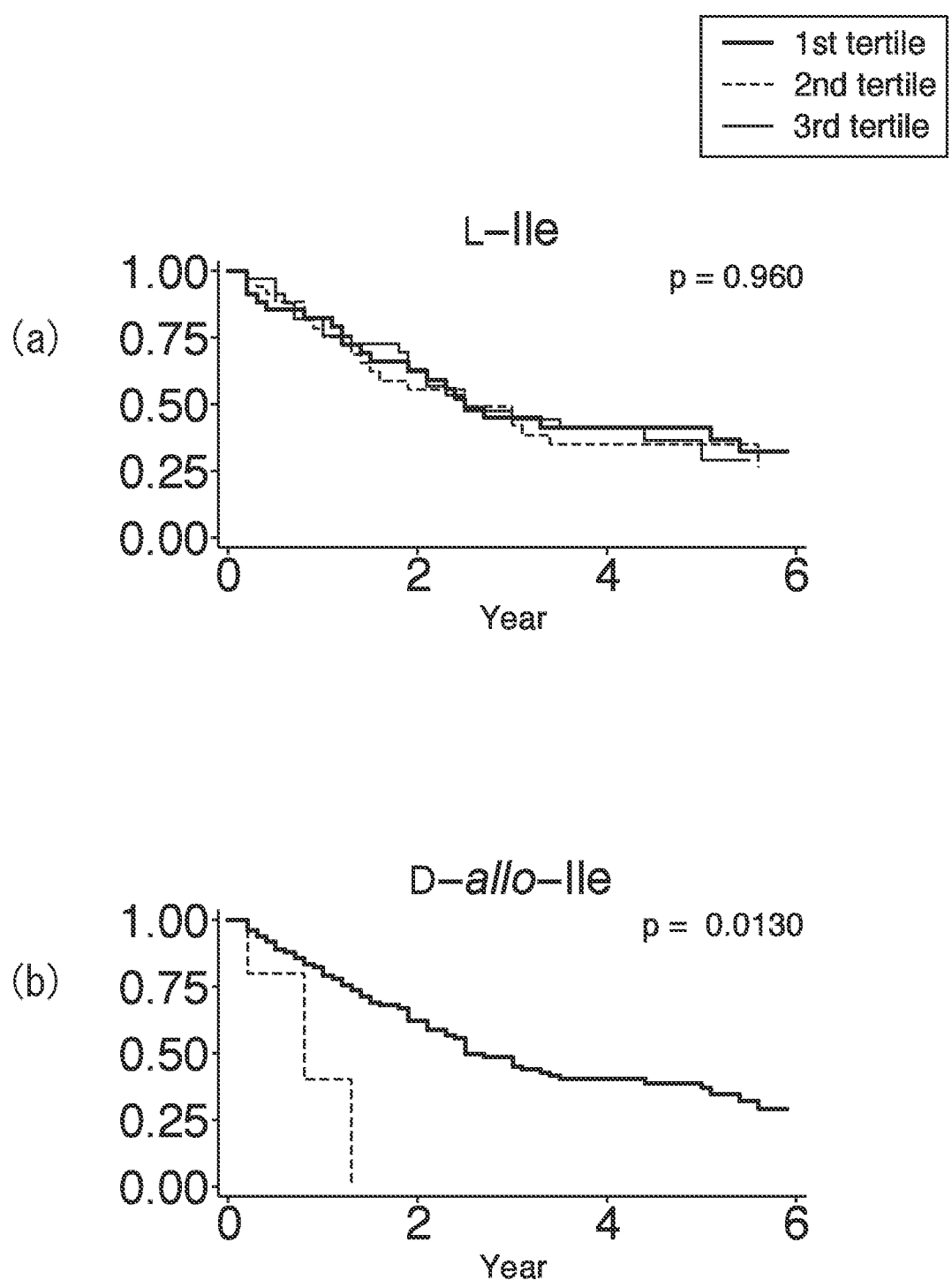
FIG. 5 indicates the results of dividing (a) amount of L-isoleucine and (b) amount of D-alloisoleucine at baseline into three tertiles among cohorts including 108 kidney disease patients and subjecting prognoses thereof to a Kaplan-Meier analysis.
Figure 6:
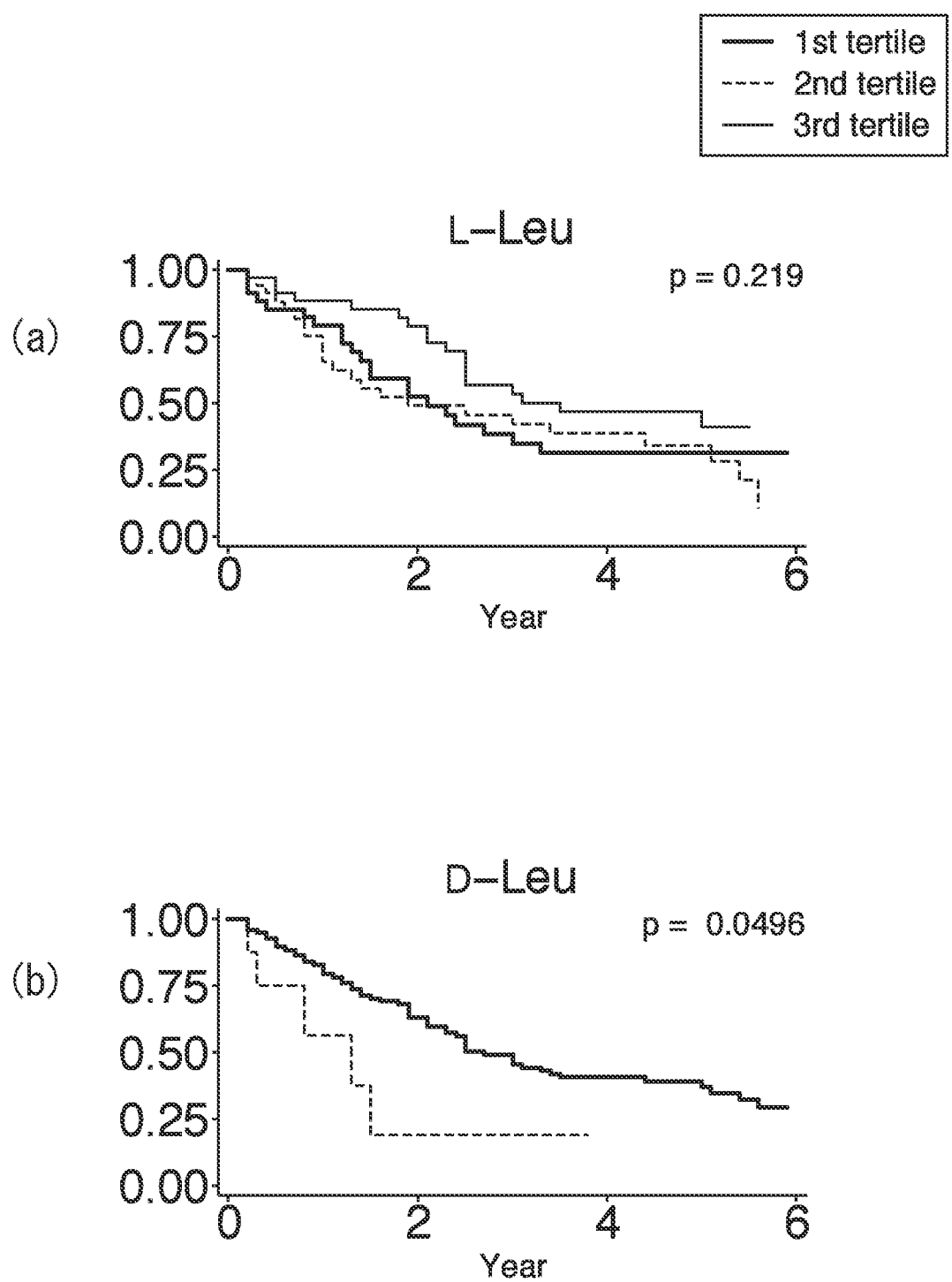
FIG. 6 indicates the results of dividing (a) amount of L-leucine and (b) amount of D-leucine at baseline into three tertiles among cohorts including 108 kidney disease patients and subjecting prognoses thereof to a Kaplan-Meier analysis.
Figure 7:
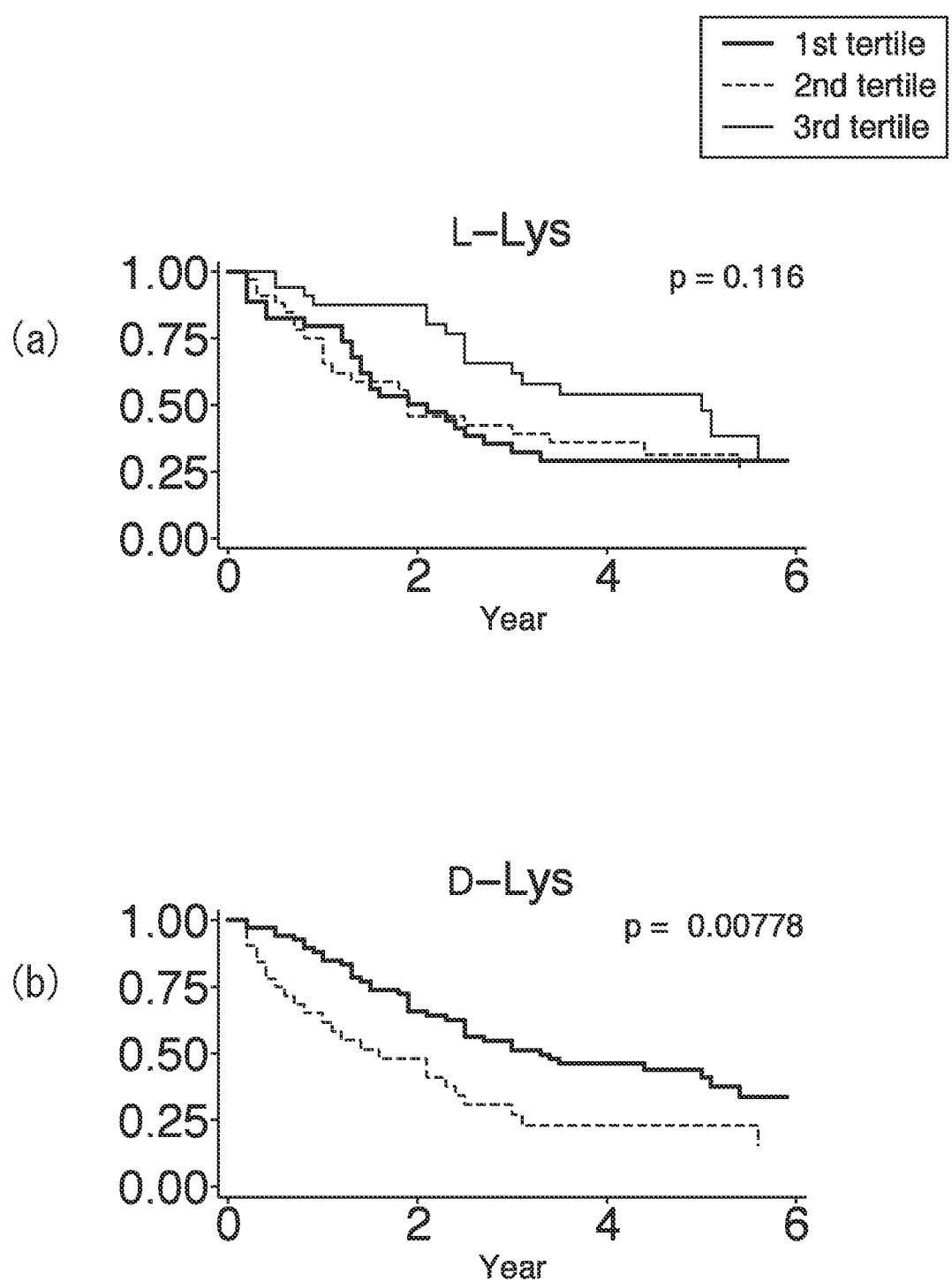
FIG. 7 indicates the results of dividing (a) amount of L-lysine and (b) amount of D-lysine at baseline into three tertiles among cohorts including 108 kidney disease patients and subjecting prognoses thereof to a Kaplan-Meier analysis.
Figure 8:
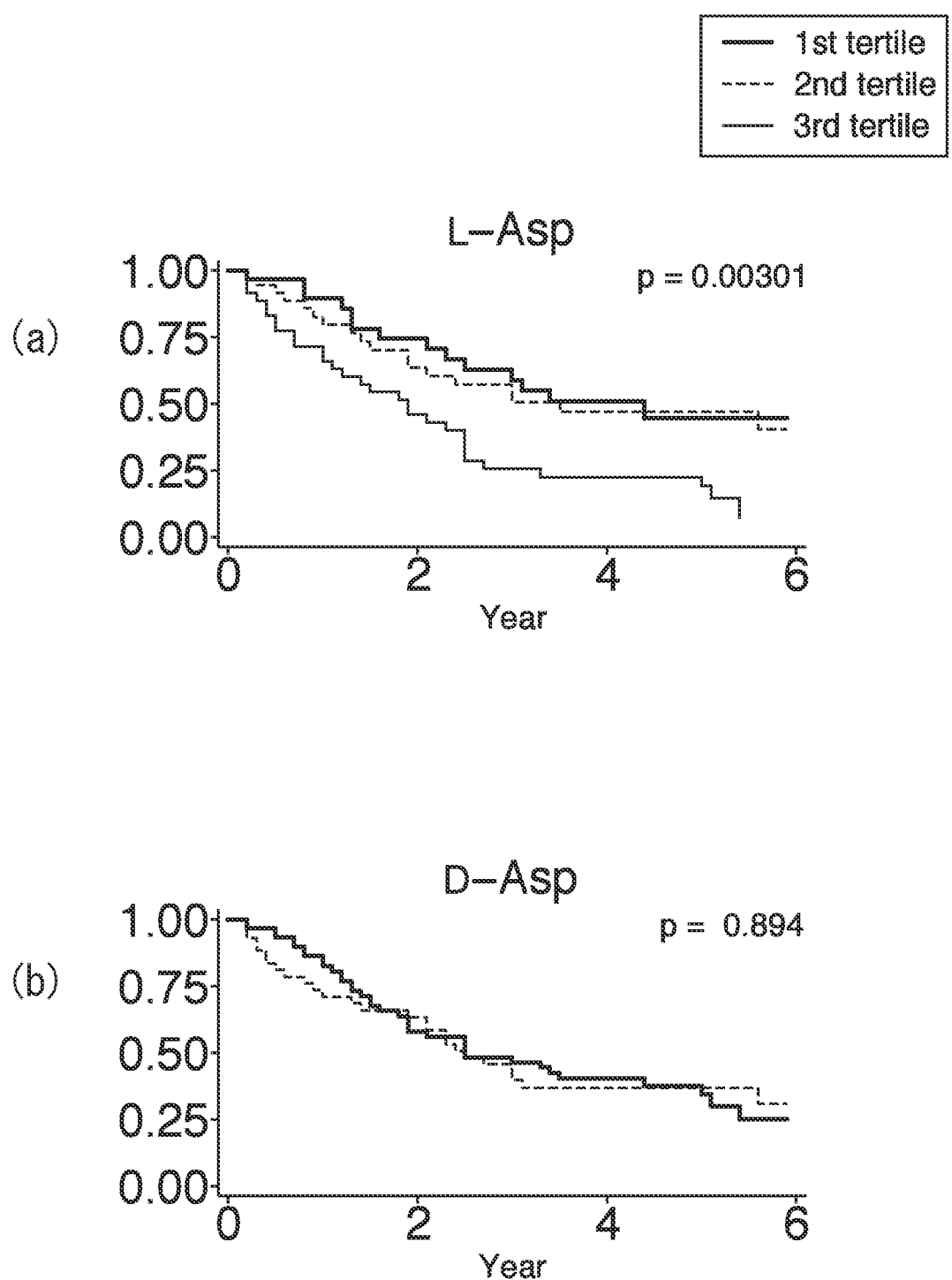
FIG. 8 indicates the results of dividing (a) amount of L-aspartic acid and (b) amount of D-aspartic acid at baseline into three tertiles among cohorts including 108 kidney disease patients and subjecting prognoses thereof to a Kaplan-Meier analysis.
Figure 9:
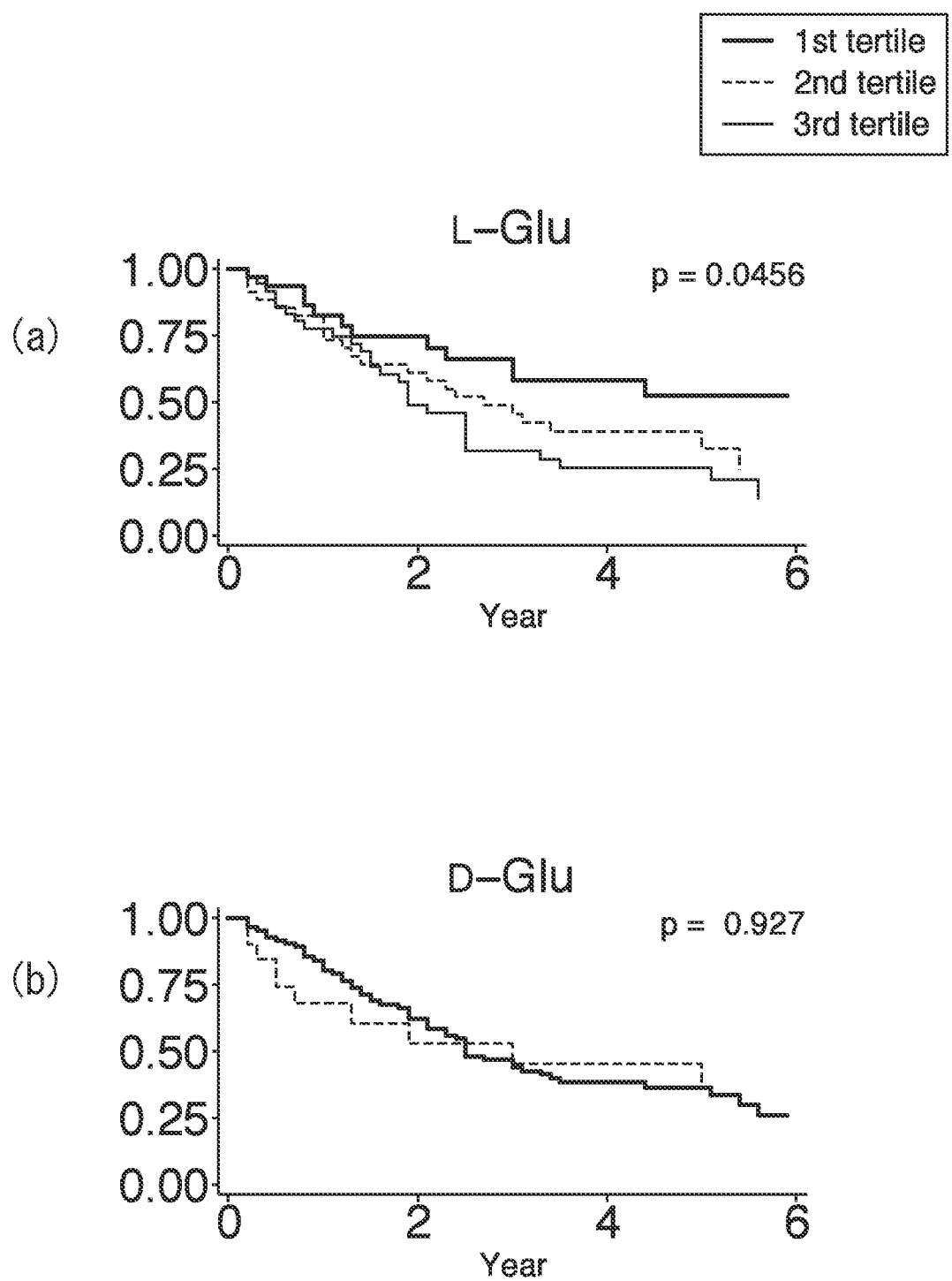
FIG. 9 indicates the results of dividing (a) amount of L-glutamic acid and (b) amount of D-glutamic acid at baseline into three tertiles among cohorts including 108 kidney disease patients and subjecting prognoses thereof to a Kaplan-Meier analysis.
Figure 10:
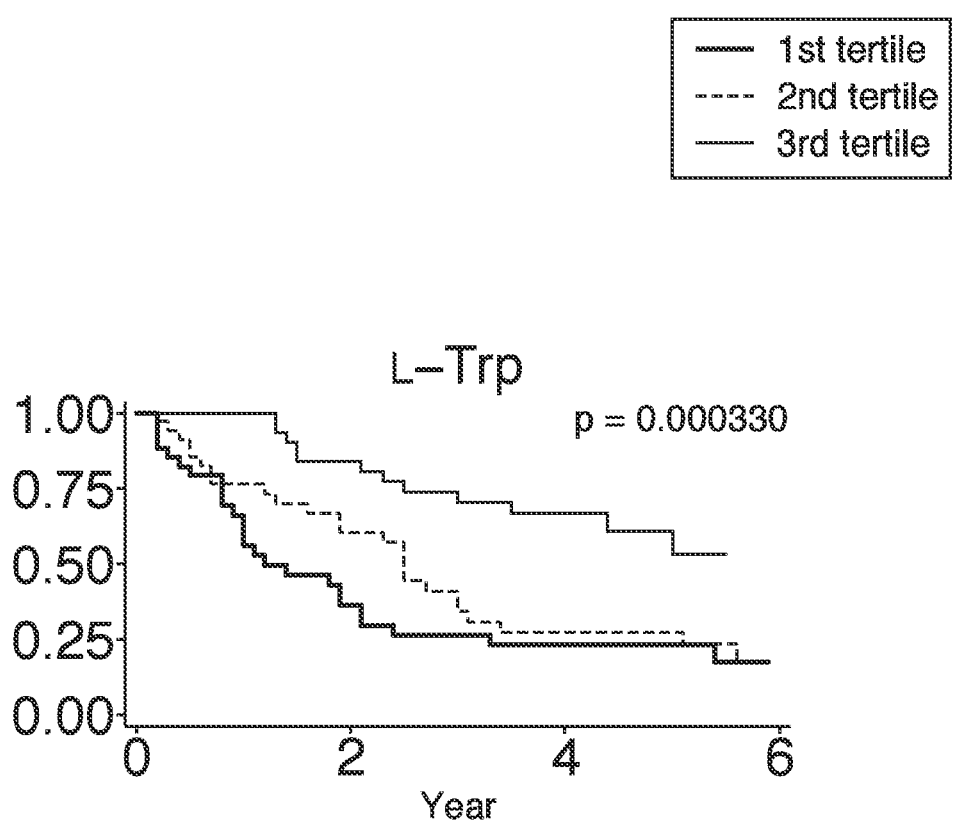
FIG. 10 indicates the results of dividing amount of L-tryptophan at baseline into three tertiles among cohorts including 108 kidney disease patients and subjecting prognoses thereof to a Kaplan-Meier analysis.
Figure 11:
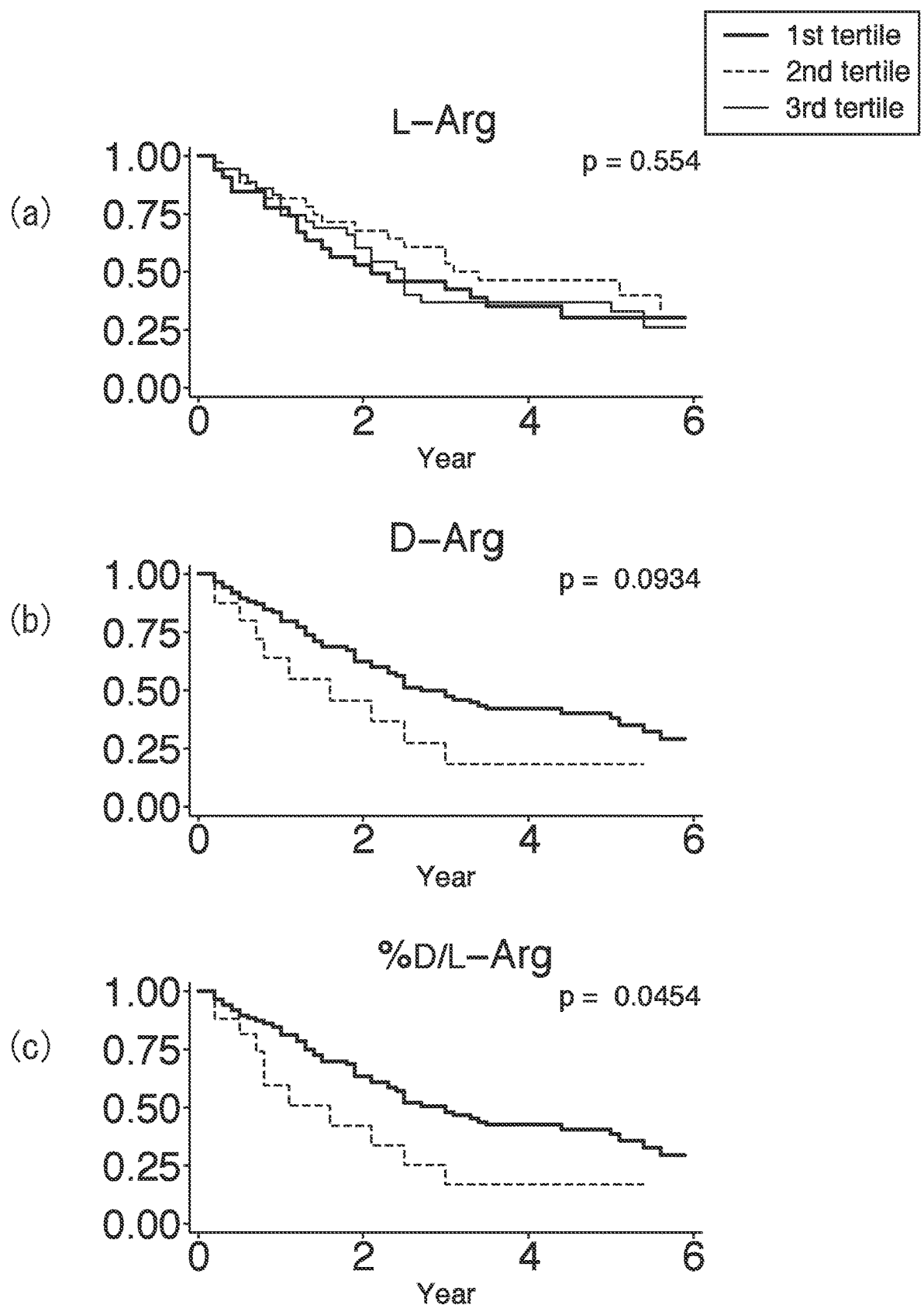
FIG. 11 indicates the results of dividing (a) amount of L-arginine, (b) amount of D-arginine and (c) ratio of D-arginine/L-arginine at baseline into three tertiles among cohorts including 108 kidney disease patients and subjecting prognoses thereof to a Kaplan-Meier analysis.
Figure 13:
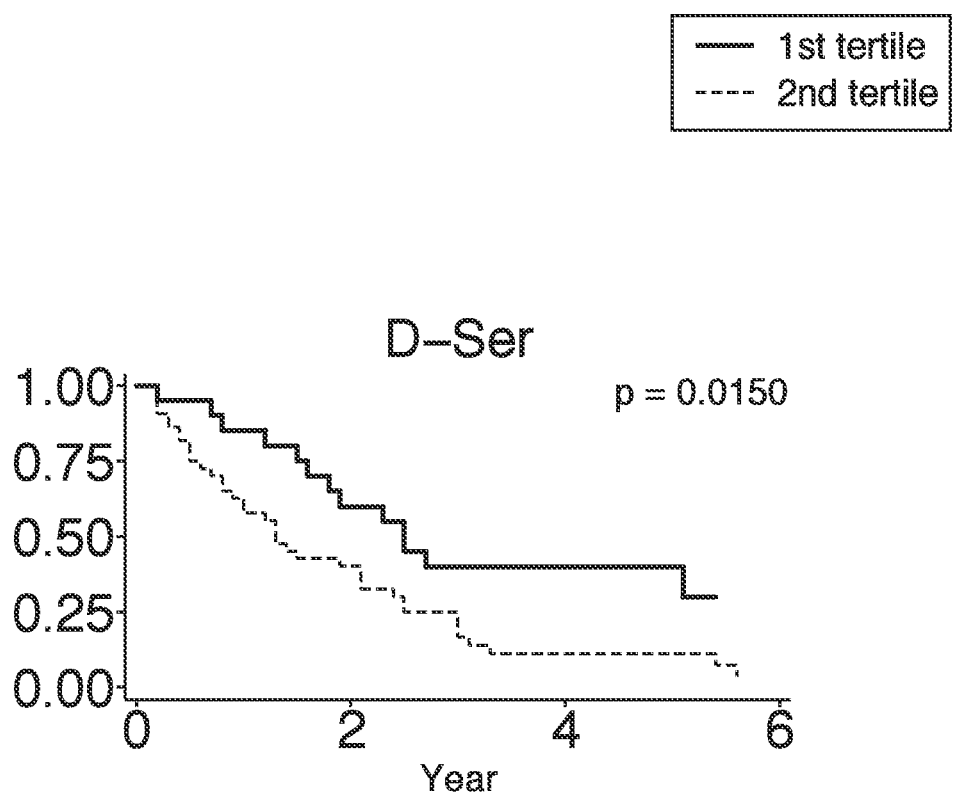
FIG. 13 indicates the results of dividing into cohorts including 66 kidney disease patients having eGFR levels of 20 ml/min/1.73 m$^2$ or less, dividing amount of D-serine at baseline among the cohorts into two tertiles, and subjecting prognoses thereof to a Kaplan-Meier analysis.

Patients presenting with high levels of all of the frequently detected amino acids of D-Ser, D-Ala, D-Pro and D-Asn as determined by Kaplan-Meier curve analysis were shown to reach kidney outcome (end-stage kidney disease requiring renal replacement therapy and death by any cause) at a higher frequency in comparison with other patient groups (FIGS. 1 to 4). In the case of having divided the patients according to renal function, although separation of kidney outcome was observed for D-Ala and D-Pro in patients having eGFR of 20 ml/min/1.73 m² (FIGS. 3 and 4), the same results were also observed for D-Ser and D-Asn (FIGS. 2 and 1). Several D-amino acids that were hardly detected at all (D-Lys, D-Leu and D-AlloIle) and several L-amino acids (L-Asp, L-Glu, L-Ala, L-Trp and L-Lys) also separated kidney prognosis (FIGS. 5 to 13).

The inventors of the present invention evaluated the correlation between frequently detected D-amino acids and kidney outcome by carrying out a multiple Cox regression analysis. According to the results of a Cox analysis used without adjusting the measured amounts, those patients belonging to the highest tertiles for D-Asn, D-Ser, D-Ala and D-Pro demonstrated hazard ratios with respect to kidney outcome that were 3.05 times to 5.68 times higher than patients belonging to the lowest tertiles (Table 2, Unadjusted Model). Patients belonging to the highest tertiles for D-Ser and D-Asn demonstrated adjusted hazard ratios with respect to kidney outcome following adjustment based on renal function and urinary protein level that were 2.7 times to 3.7 times higher than patients belonging to the lowest tertiles (Table 2, Model 1). These findings were the same even in the case of having further adjusted for such factors as age or concomitant disease such as the presence or absence of diabetes having some effect on D-amino acid levels (Table 2, Model 2). Thus, these D-amino acids were associated with the progression of kidney disease in CKD patients.

TABLE 2

| Cox Regression Analysis of Risk of Kidney Outcome for D-Amino Acids | | | | |
|---|---|---|---|---|
| D-amino acid | D-Asn | D-Ser | D-Ala | D-Pro |
| Unadjusted Model | | | | |
| 1st tertile | 1.00 (ref) | 1.00 (ref) | 1.00 (ref) | 1.00 (ref) |
| 2nd tertile | 2.37 (1.14-4.94) | 3.27 (1.5-7.13) | 1.38 (0.72-2.67) | 2.56 (1.32-4.97) |
| 3rd tertile | 5.06 (2.49-10.29) | 5.68 (2.69-11.99) | 3.11 (1.67-5.97) | 3.05 (1.57-5.93) |
| Model 1 | | | | |
| 1st tertile | 1.00 (ref) | 1.00 (ref) | 1.00 (ref) | 1.00 (ref) |
| 2nd tertile | 1.82 (0.85-3.94) | 1.62 (0.7-3.73) | 0.78 (0.4-1.53) | 1.51 (0.76-3) |
| 3rd tertile | 3.76 (1.74-8.09) | 2.81 (1.23-6.37) | 1.28 (0.66-2.5) | 1.38 (0.68-2.79) |
| Model 2 | | | | |
| 1st tertile | 1.00 (ref) | 1.00 (ref) | 1.00 (ref) | 1.00 (ref) |
| 2nd tertile | 1.54 (0.69-3.44) | 1.3 (0.54-3.09) | 0.98 (0.48-2) | 1.60 (0.8-3.21) |
| 3rd tertile | 3.07 (1.3-7.26) | 2.49 (1-6.19) | 1.41 (0.71-2.79) | 1.57 (0.79-3.11) |

Model generated by adjusting for eGFR and urinary protein
Model generated by adjusting for eGFR, urinary protein level, diabetes, age, gender, hemoglobin level, mean blood pressure, history of cardiovascular events, treatment with anti-hypertensive drugs Values indicated as hazard ratios (95% CI).

The invention claimed is:

1. A method for prognosing an end stage kidney disease requiring renal replacement and treating a subject who has a prognosis of the end stage kidney disease and who has not been subjected to a dialysis, comprising:
   measuring an amount of at least one D-amino acid selected from the group consisting of D-serine, D-asparagine, D-proline, D-alanine, D-leucine, D-lysine, D-allo-isoleucine in a blood sample of the subject,
   measuring an amount of one or more of creatinine, urinary protein and cystatin C in the subject;
   and
   correlating (a) an index value based on the measured amount of the at least one D-amino acid according to a cutoff value for the index value and (b) the measured amount of the one or more of creatinine, urinary protein and cystatin C with a prognosis of the end stage kidney disease for the subject;
   identifying the subject with (a) the index value based on the measured amount of the at least one D-amino acid being higher than the cutoff value for the respective D-amino acid and (b) the measured amount of the one or more of creatinine, urinary protein and cystatin C indicating the end stage kidney disease as a subject with a prognosis for the end stage kidney disease; and
   administering to the subject with the prognosis for the end stage kidney disease
      a treatment selected from the group consisting of dialysis, kidney transplant, lifestyle improvement, dietary counseling, blood pressure management, blood sugar management and lipid management.

2. The method according to claim 1, wherein the cutoff value is predetermined by a Kaplan-Meier curve analysis.

3. The method according to claim 2, wherein the cutoff value is 5.6 µmol/L for D-serine, 0.7 µmol/L for D-asparagine, 4.7 µmol/L for D-proline, 5.2 µmol/L for D-alanine, 0.5 µmol/L for D-leucine, 0.6 µmol/L for D-lysine, 0.1 µmol/L for D-alloisoleucine.

4. The method according to claim 1, further comprising measuring an amount of an isomer corresponding to the at least one D-amino acid, wherein the index value is the ratio of the amount of the at least one D-amino acid to the amount of the corresponding isomer.

5. The method according to claim 1, wherein the index value is further adjusted for one or more variables selected from the group consisting of eGFR, urinary protein level, diabetes, age, gender, hemoglobin level, mean blood pressure, history of cardiovascular events and presence or absence of anti-hypertensive drug treatment.

6. The method according to claim 1, wherein said administering comprises administering to the subject with the prognosis for the end stage kidney disease an ACE inhibitor or ARB.

7. The method according to claim 1, wherein said administering comprises administering to the subject with the prognosis for the end stage kidney disease insulin.

8. The method according to claim 1, wherein said administering comprises administering to the subject with the prognosis for the end stage kidney disease a hyperlipidemia drug.

9. A method for prognosing an end stage kidney disease requiring renal replacement and treating a subject who has a prognosis of the end stage kidney disease and who has not been subjected to a dialysis, comprising:
    measuring an amount of each of D-serine, D-asparagine, D-proline, and D-alanine in a blood sample of the subject, and
    correlating an index value based on the measured amount of each of D-serine, D-asparagine, D-proline, and D-alanine with a prognosis of the end stage kidney disease for the subject according to a cutoff value for the index value,
    identifying the subject with the index value based on the measured amount of each of D-serine, D-asparagine, D-proline, and D-alanine being higher than the respective cutoff value for D-serine, D-asparagine, D-proline, and D-alanine as a subject with a prognosis for the end stage kidney disease; and
    administering to the subject with the prognosis for the end stage kidney disease a treatment selected from the group consisting of dialysis, kidney transplant, lifestyle improvement, dietary counseling, blood pressure management, blood sugar management and lipid management.

10. The method of claim 9, wherein said administering comprises administering to the subject with the prognosis for the end stage kidney disease an ACE inhibitor or ARB.

11. The method of claim 9, wherein said administering comprises administering to the subject with the prognosis for the end stage kidney disease insulin.

12. The method of claim 9, wherein said administering comprises administering to the subject with the prognosis for the end stage kidney disease a hyperlipidemia drug.

13. The method of claim 9, wherein the cutoff value is predetermined by a Kaplan-Meier curve analysis.

14. The method of claim 13, wherein the cutoff value is 5.6 µmol/L for D-serine, 0.7 µmol/L for D-asparagine, 4.7 µmol/L for D-proline, 5.2 µmol/L for D-alanine, 0.5 µmol/L for D-leucine, 0.6 µmol/L for D-lysine, 0.1 µmol/L for D-alloisoleucine.

15. The method of claim 1, comprising measuring an amount of creatinine in the subject, wherein said correlating comprises correlating (a) the index value based on the measured amount of the at least one D-amino acid according to the cutoff value for the index value and (b) the measured amount of creatinine with the prognosis of the end stage kidney disease for the subject and said identifying is identifying the subject with (a) the index value based on the measured amount of the at least one D-amino acid being higher than the cutoff value for the respective D-amino acid and (b) the measured amount of creatinine indicating the end stage kidney disease as a subject with a prognosis for the end stage kidney disease.

16. The method of claim 1, comprising measuring an amount of urinary protein in the subject, wherein said correlating comprises correlating (a) the index value based on the measured amount of the at least one D-amino acid according to the cutoff value for the index value and (b) the measured amount of urinary protein with the prognosis of the end stage kidney disease for the subject and said identifying is identifying the subject with (a) the index value based on the measured amount of the at least one D-amino acid being higher than the cutoff value for the respective D-amino acid and (b) the measured amount of urinary protein indicating the end stage kidney disease as a subject with a prognosis for the end stage kidney disease.

17. The method of claim 1, comprising measuring an amount of cystatin C in the subject, wherein said correlating comprises correlating (a) the index value based on the measured amount of the at least one D-amino acid according to the cutoff value for the index value and (b) the measured amount of cystatin C with the prognosis of the end stage kidney disease for the subject and said identifying is identifying the subject with (a) the index value based on the measured amount of the at least one D-amino acid being higher than the cutoff value for the respective D-amino acid and (b) the measured amount of cystatin C indicating the end stage kidney disease as a subject with a prognosis for the end stage kidney disease.

18. The method of claim 9, further comprising measuring an amount of at least one creatinine, urinary protein and cystatin C in the subject, wherein said correlating comprises correlating (a) the index value based on the measured amount of each of D-serine, D-asparagine, D-proline, and D-alanine according to the cutoff value for the index value and (b) the measured amount of the one or more of creatinine, urinary protein and cystatin C with the prognosis of the end stage kidney disease for the subject; and said identifying comprises identifying the subject with (a) the index value based on the measured amount of each of D-serine, D-asparagine, D-proline, and D-alanine being higher than the respective cutoff value for D-serine, D-asparagine, D-proline, and D-alanine and (b) the measured amount of the one or more of creatinine, urinary protein and cystatin C indicating the end stage kidney disease as a subject with a prognosis for the end stage kidney disease.

19. The method of claim 18, comprising measuring an amount of creatinine in the subject, wherein said correlating comprises correlating (a) the index value based on the measured amount of each of D-serine, D-asparagine, D-proline, and D-alanine according to the cutoff value for the index value and (b) the measured amount of creatinine with the prognosis of the end stage kidney disease for the subject; and said identifying comprises identifying the subject with (a) the index value based on the measured amount of each of D-serine, D-asparagine, D-proline, and D-alanine being higher than the respective cutoff value for D-serine, D-asparagine, D-proline, and D-alanine and (b) the measured amount of creatinine indicating the end stage kidney disease as a subject with a prognosis for the end stage kidney disease.

20. The method of claim 18, comprising measuring an amount of urinary protein in the subject, wherein said correlating comprises correlating (a) the index value based on the measured amount of each of D-serine, D-asparagine, D-proline, and D-alanine according to the cutoff value for the index value and (b) the measured amount of urinary protein with the prognosis of the end stage kidney disease for the subject; and said identifying comprises identifying the subject with (a) the index value based on the measured amount of each of D-serine, D-asparagine, D-proline, and D-alanine being higher than the respective cutoff value for D-serine, D-asparagine, D-proline, and D-alanine and (b) the measured amount of urinary protein indicating the end stage kidney disease as a subject with a prognosis for the end stage kidney disease.

21. The method of claim 18, comprising measuring an amount of cystatin C in the subject, wherein said correlating comprises correlating (a) the index value based on the measured amount of each of D-serine, D-asparagine, D-proline, and D-alanine according to the cutoff value for the index value and (b) the measured amount of cystatin C with the prognosis of the end stage kidney disease for the subject; and said identifying comprises identifying the subject with (a) the index value based on the measured amount of each of D-serine, D-asparagine, D-proline, and D-alanine being higher than the respective cutoff value for D-serine, D-asparagine, D-proline, and D-alanine and (b) the measured amount of cystatin C indicating the end stage kidney disease as a subject with a prognosis for the end stage kidney disease.

* * * * *